(12) United States Patent
Lamberti et al.

(10) Patent No.: US 9,610,382 B2
(45) Date of Patent: *Apr. 4, 2017

(54) IMMOBILIZED BIOACTIVE HYDROGEL MATRICES AS SURFACE COATINGS

(71) Applicant: Pioneer Surgical Technology, Inc., Marquette, MI (US)

(72) Inventors: Francis Vincent Lamberti, Cary, NC (US); Richard Chris Klann, Washington, NC (US); Ronald Stewart Hill, Greenville, NC (US)

(73) Assignee: RTI Surgical, Inc., Marquette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/074,296

(22) Filed: Nov. 7, 2013

(65) Prior Publication Data

US 2014/0066694 A1 Mar. 6, 2014

Related U.S. Application Data

(63) Continuation of application No. 11/937,851, filed on Nov. 9, 2007, now Pat. No. 8,609,122, which is a (Continued)

(51) Int. Cl.
*C08L 5/02* (2006.01)
*C08L 89/00* (2006.01)
(Continued)

(52) U.S. Cl.
CPC .......... *A61L 27/222* (2013.01); *A61F 2/0063* (2013.01); *A61K 47/42* (2013.01);
(Continued)

(58) Field of Classification Search
CPC .. C08L 5/02; C08L 89/00; A61L 27/26; A61L 27/34; A61L 31/10; A61L 2300/112;
(Continued)

(56) References Cited

U.S. PATENT DOCUMENTS 4,446,316 A 5/1984 Chazov et al.
4,520,821 A 6/1985 Schmidt et al.
(Continued)

FOREIGN PATENT DOCUMENTS

EP 0 213 908 3/1987
EP 0 544 259 6/1993
(Continued)

OTHER PUBLICATIONS

Wikipedia, Polyethylene Terephthalate, accessed May 1, 2014, pp. 1-14.*
(Continued)

*Primary Examiner* — Ernst V Arnold
(74) *Attorney, Agent, or Firm* — Womble Carlyle Sandridge & Rice, LLP

(57) ABSTRACT

The present invention is directed to a stabilized bioactive hydrogel matrix coating for substrates, such as medical devices. The invention provides a coated substrate comprising a substrate having a surface, and a bioactive hydrogel matrix layer overlying the surface of the medical device, the hydrogel matrix comprising a first high molecular weight component and a second high molecular weight component, the first and second high molecular weight components each being selected from the group consisting of polyglycans and polypeptides, wherein at least one of the first and second high molecular weight components is immobilized (e.g., by covalent cross-linking) to the surface of the substrate.

9 Claims, 9 Drawing Sheets

Related U.S. Application Data continuation of application No. 10/372,757, filed on Feb. 21, 2003, now Pat. No. 7,303,814.

(60) Provisional application No. 60/358,625, filed on Feb. 21, 2002.

(51) Int. Cl.

| | | |
|---|---|---|
| *A61L 27/34* | (2006.01) | |
| *A61L 27/20* | (2006.01) | |
| *A61L 27/22* | (2006.01) | |
| *A61L 27/26* | (2006.01) | |
| *A61L 27/52* | (2006.01) | |
| *A61L 31/10* | (2006.01) | |
| *A61L 27/02* | (2006.01) | |
| *A61L 27/12* | (2006.01) | |
| *A61L 27/36* | (2006.01) | |
| *A61F 2/00* | (2006.01) | |
| *A61K 47/42* | (2017.01) | |
| *A61L 27/24* | (2006.01) | |
| *A61L 27/54* | (2006.01) | |
| *B29C 39/00* | (2006.01) | |
| *A61K 31/728* | (2006.01) | |
| *A61K 47/36* | (2006.01) | |
| *B29L 31/00* | (2006.01) | |

(52) U.S. Cl.
CPC .............. *A61L 27/025* (2013.01); *A61L 27/12* (2013.01); *A61L 27/20* (2013.01); *A61L 27/22* (2013.01); *A61L 27/24* (2013.01); *A61L 27/26* (2013.01); *A61L 27/34* (2013.01); *A61L 27/3608* (2013.01); *A61L 27/52* (2013.01); *A61L 27/54* (2013.01); *A61L 31/10* (2013.01); *B29C 39/003* (2013.01); *A61L 2300/112* (2013.01); *A61L 2300/412* (2013.01); *A61L 2430/02* (2013.01); *B29L 2031/7532* (2013.01); *Y10T 428/29* (2015.01); *Y10T 428/2947* (2015.01); *Y10T 428/31551* (2015.04); *Y10T 428/31786* (2015.04)

(58) Field of Classification Search
CPC ........... A61L 2300/412; A61L 2430/02; A61L 27/025; A61L 27/12; A61L 27/20; A61L 27/22; A61L 27/222; A61L 27/24; A61L 27/03; A61L 27/52; A61L 27/54; A61F 2/0063; A61K 47/42; B29C 39/003; B29L 2031/7532; D05B 3/08; Y10T 428/29; Y10T 428/2947; Y10T 428/31551; Y10T 428/31786

See application file for complete search history.

(56) References Cited

U.S. PATENT DOCUMENTS

| | | | |
|---|---|---|---|
| 4,563,350 A | 1/1986 | Nathan et al. | |
| 4,618,490 A | 10/1986 | De Marco | |
| 4,772,468 A | 9/1988 | Pfirrmann | |
| 4,863,856 A | 9/1989 | Dean, Jr. et al. | |
| 4,883,487 A | 11/1989 | Yoshizato et al. | |
| 4,895,724 A | 1/1990 | Cardinal et al. | |
| 4,902,295 A | 2/1990 | Walthall et al. | |
| 4,950,483 A | 8/1990 | Ksander et al. | |
| 4,957,902 A | 9/1990 | Grinnell | |
| 4,997,753 A | 3/1991 | Dean, Jr. et al. | |
| 5,099,012 A | 3/1992 | Wu et al. | |
| 5,100,783 A | 3/1992 | Dean, Jr. et al. | |
| 5,263,983 A | 11/1993 | Yoshizato et al. | |
| 5,290,558 A | 3/1994 | O'Leary et al. | |
| 5,303,718 A | 4/1994 | Krajicek | |
| 5,350,583 A | 9/1994 | Yoshizato et al. | |
| 5,457,093 A | 10/1995 | Cini et al. | |
| 5,470,911 A | 11/1995 | Rhee et al. | |
| 5,484,601 A | 1/1996 | O'Leary et al. | |
| 5,591,709 A | 1/1997 | Lindenbaum | |
| 5,605,938 A | 2/1997 | Roufa et al. | |
| 5,614,205 A | 3/1997 | Usala | |
| 5,645,591 A | 7/1997 | Kuberasampath et al. | |
| 5,705,485 A | 1/1998 | Cini et al. | |
| 5,707,877 A | 1/1998 | Siiman et al. | |
| 5,716,404 A | 2/1998 | Vacanti et al. | |
| 5,718,012 A | 2/1998 | Cavallaro | |
| 5,733,337 A | 3/1998 | Carr, Jr. et al. | |
| 5,756,715 A | 5/1998 | Monte et al. | |
| 5,783,214 A | 7/1998 | Royer | |
| 5,824,331 A | 10/1998 | Usala | |
| 5,830,492 A | 11/1998 | Usala | |
| 5,830,879 A * | 11/1998 | Isner | 514/44 R |
| 5,834,005 A | 11/1998 | Usala | |
| 5,866,165 A | 2/1999 | Liu et al. | |
| 5,885,647 A | 3/1999 | Larm et al. | |
| 5,922,339 A | 7/1999 | Usala | |
| 5,972,385 A | 10/1999 | Liu et al. | |
| 5,993,844 A | 11/1999 | Abraham et al. | |
| 6,011,008 A | 1/2000 | Domb et al. | |
| 6,077,916 A | 6/2000 | Laurencin et al. | |
| 6,132,759 A * | 10/2000 | Schacht et al. | 424/445 |
| 6,165,488 A | 12/2000 | Tardy et al. | |
| 6,197,330 B1 | 3/2001 | Rees et al. | |
| 6,231,881 B1 | 5/2001 | Usala et al. | |
| 6,261,587 B1 | 7/2001 | Usala | |
| 6,299,448 B1 | 10/2001 | Zdrahala et al. | |
| 6,303,585 B1 | 10/2001 | Spiro et al. | |
| 6,352,707 B1 | 3/2002 | Usala | |
| 6,391,052 B2 | 5/2002 | Buirge et al. | |
| 6,458,386 B1 | 10/2002 | Schacht et al. | |
| 6,471,993 B1 | 10/2002 | Shastri et al. | |
| 6,582,472 B2 * | 6/2003 | Hart | 623/23.7 |
| 2002/0019516 A1 | 2/2002 | Noff et al. | |
| 2002/0049281 A1 | 4/2002 | Zhao et al. | |

FOREIGN PATENT DOCUMENTS

| | | |
|---|---|---|
| WO | WO 92/19195 | 11/1992 |
| WO | WO 95/14037 | 5/1995 |
| WO | WO 00/02600 | 1/2000 |
| WO | WO 01/74411 | 10/2001 |
| WO | WO 02/39948 | 5/2002 |

OTHER PUBLICATIONS

Anderson, V, and Jones, R., "The Influence of Gelatin on the Mechanism of Phase Separation of a Biopolymer Mixture," *Polymer*, 2001, pp. 9601-9610, vol. 42, Elsevier Science Ltd.

Antonov, Y. and Zubova, O., "Phase State of Aqueous Gelatin-Polysaccharaide (1)-Polysaccharide (2) Systems," *International Journal of Biological Marcomolecules*, 2001, pp. 67-71, vol. 29, Elsevier Science Ltd., B.V.

Arnold, P., et al., "Evaluation of Resorbable Barriers for Preventing Surgical Adhesions," *Fertility and Sterility*, 2000, pp. 157-161, vol. 72(1), Elsevier Science Inc.

Aso, Y., et al., "Thermally Controlled Protein Release From Gelatin-Dextran Hydrogels," *Radiation Physics and Chemistry*, 1999, pp. 179-183, vol. 55, Elsevier Science Ltd.

Ayhan, F., et al., "Optimization of Urease Immobilization onto Non-Porous HEMA Incorporated Poly(EGDMA) Microbeads and Estimation of Kinetic Parameters," *Bioresource Technology*, 2002, pp. 131-140, vol. 81, Elsevier Science Ltd.

Bae, J.S., et al., "Synthesis and Characterization of Harparinized Polyurethanes Using Plasma Glow Discharge," *Biomaterials*, 1999, pp. 529-537, vol. 20(6).

Bailey, Al and Light, N.D., "Intermolecular Cross-Linking in Fibrotic Collagen," *Ciba Found Symp.*, 1985, pp. 80-96, vol. 114.

Barié, N., etal., "Covalent Photolinker-Mediated Immobilization of an Intermediate Dextran Layer to Polymer-Coated Surfaces for

(56) References Cited

OTHER PUBLICATIONS

Biosensing Applications," *Biosensors & Bioelectronics*, 1998, pp. 855-860, vol. 13, Elsevier Science S.A.

Barker, H., et al., "Formaldehyde as a Pre-Treatment of Dermal Collagen Heterografts," *Biochimica et Biophysica Acta*, 1980, pp. 589-597, vol. 632.

Ben Slimane, S., et al., Characteristics of Polyester Arterial Grafts Coated with Albumin, the Role and the Importance of the Crosslinking Chemicals, *Eur. Surg. Res.*, 1988, pp. 18-28, vol. 20.

Bisson, I., et al., "Acrylic Acid Grafting and Collagen Immobilization on Poly(ethylene terephthalate) Surfaces for Adherence and Growth of Human Bladder and Smooth Muscle Cells," *Biomaterials*, 2002, pp. 3149-3158, vol. 23, Elsevier Science Ltd.

Bos, G.W., etal., "Proliferation of Endothelial Cells on Surface-Immobilized Albumin-Heparin Conjugate Loaded with Basic Fibroblast Growth Factor," *J. Biomed. Mater. Res.*, 1999, pp. 330-340, vol. 44, John Wiley & Sons, Inc.

Boyan, B.D. et al., "Role of Material Surfaces in Regulating Bone and Cartilage Cell Response," *Biomaterials*, 1996, pp. 137-146, vol. 17.

Boyce, S.T. and Hansborough, J,F., Biologic Attachment, Growth, and Differentiation of Cultured Human Epidermal Keratinocytes on a Graftable Collagen and chondroitin-6-sulfate substrate, *Surgery*, 1988, pp. 421-431, vol. 103.

Bubnis, W.A. And Ofner C.M. III, "The Determination of c-Amino Groups in Soluble and Poorly Soluble Proteinaceous Materials by a Spectrophotometric Method Using Trinitrobezenesulfonic Acid," *Anal. Biochem*, 1992, pp. 129-133, vol. 207.

Bulgarelli, E., etal., "Casein/Gelatin Beads: I. Cross-Linker Solution Composition Effect on Cross-Linking Degree," 1999, *Int. J. Pharm.*, 1999, pp. 175-182, vol. 190(2).

Butler, C., et al., "Regeneration of Neomucosa Using Cell-Seeded Collagen-GAG Matrices in Athymic Mice," *Annals of Plastic Surgery*, 2002, pp. 298-304, vol. 48, Lippincott Williams & Wilkins, Inc.

Calero, P., et al., "Gelatinases in Soft Tissue Biomaterials, Analysis of Different Crosslinking Agents," *Biomaterials*, 2002, pp. 3473-3478, vol. 23, Elsevier Science Ltd.

Cao, X. and Shoichet, M., "Photoimmobilization of Biomolecules within a 3-Dimensional Hydrogel Matrix," *J. Biomater. Sci. Polymer Edn.*, 2002, pp. 623-636, vol. 13(6).

Chandy, T., et al., "Use of Plasma Glow for Surface-Engineering Biomolecules to Enhance Bloodcompatibility of Dacron and PTFE Vascular Prosthesis," *Biomaterials*, 2000, pp. 699-712, vol. 21, Elsevier Science Ltd.

Charulatha, V. and Rajaram, a., "Crosslinking Density and Resorption of Dimethyl Subermimidate-Treated Collagen," *J. Biomed. Mater. Res.* 1997, pp. 478-486, vol. 15.

Charulatha, V. and Rajaram, A., "Dimethyl 3,3'-dithiobispropionimidate: A Novel Crosslinking Reagent for Collagen," J. Biomed. Mater. Res., 2001, pp. 122-128, vol. 54.

Chegel, V., et al., "A Novel Aldehyde Dextran Sulfonate Matrix for Affinity Biosensors," *J. Biochem. Biophys. Methods*, 2002, pp. 201-216, vol. 50, Elsevier Science B.V.

Chen, T., et al., "In Vitro Protein-Polysaccharide Conjugation: Tyrosinase-Catalyzed Conjugation of Gelatin and Chitosan," *Biopolymers*, 2002, pp. 292-302, vol. 64, Wiley Periodicals, Inc.

Chevolot, Y,, et al., "Immobilisation on Polystyrene of Diazirine Derivatives of Mono-and Disaccharides: Biological Activities of Modified Surfaces," *Bioorganic & Medicinal Chemistry*, 2001, pp. 2943-2953, vol. 9, Elsevier Science Ltd.

Choi, Y., et al., "Study on Gelatin-Containing Artificial Skin: I. Preparation and Characteristics of Novel Gelatin-Alginate Sponge," *Biomaterials*, 1999, pp. 409-417, vol. 20, Elsevier Science Ltd.

Choi, Y., etal., "Studies on Gelatin-Containing Artificial Skin: II, Preparation and Characterization of Cross-Linked Gelatin-Hyaluronate Sponge," *J. Biomed. Mater. Res. (Appl. Biomater.)* 1999, pp. 631- 639, vol. 48, John Wiley & Sons, Inc.

Chowdhury, D.K. and Mitra, A. K., "Kinetics of In Vitro Release of a Model Nucleoside Deoxyruridine from Crosslinked Insoluble Collagen and Collagen-Gelatin Microspheres," *International Journal of Pharmaceutics*, 1999, pp. 113-122, vol. 193.

Chu, P., et al., "Plasma-Surface Modification of Biomaterials," *Materials Science and Engineering R*, 2002, pp. 143-206, vol. 36, Elsevier Science B.V.

Cloos, P. and Christgau, S., "Non-Enzymatic Covalent Modifications of Proteins: Mechanisms, Physiological Consequences and Clinical Applications," *Matrix Biology*, 2002, pp. 39-52, vol. 21, Elsevier Science B.V.

Cortesi, R., et al., "Dextran Cross-Linked Gelatin Microspheres as a Drug Delivery System," *Eur J. Pharm. Biopharm.*, 1999, pp. 153-160, vol. 47.

Cortesi, R., et al., "Sugar Cross-Linked Gelatin for Controlled Release: Microspheres and Disks," *Biomaterials*, 1998, pp. 1641-1649, vol. 19, Elsevier Science Ltd.

Crescenzi, V., etal., "New Gelatin-Based Hydrogels Via Enzymatic Networking," *Biomacromolecules*, 2002, pp. 1384-1391, vol. 3, American Chemical Society.

Dal L., et al., "Biomedical Coatings by the Covalent Immobilization of Polysaccharides onto Gas- Plasma-Activated Polymer Surfaces," *Surface and Interface Analysis*, 2000, pp. 46-55, vol. 29, John Wiley & Sons, Ltd.

Dean et al., "Chapter 1. Matrix Preparations and Applications," in *Affinity Chromatophraphy: A Practical Approach*, 1985, IRL Press.

Dean et al., "Chapter 2, Activation Procedures," in *Affinity Chromatophraphy: A Practical Approach*, 1985, IRL Press.

Dean et al., "Chapter 3. Cross-Linking Agents for Coupling Matrices to Spacers," in *Affinity Chromatophraphy: A Practical Approach*, 1985, IRL Press.

De Kruif, C. and Tuinier, R., "Polysaccharide Protein Interactions," *Food Hydrocolloids*, 2001, pp. 555-563, vol. 15, Elsevier Science Ltd.

Denuziere, a., etal., "Chitosan-Chondroitin Sulfate and Chitosan-Hyaluronate Polyelectrolyte Complexes: Biological Properties," *Biomaterials*, 1998, pp. 1275-1285, vol. 19, Elsevier Science Ltd.

Denuziere, A., et al., "Chitosan-Chondroitin Sulfate and Chitosan-Hyaluronate Polyelectrolyte Complexes: Physico-Chemical Aspects," *Carbohydrate Polymers*, 1996, pp. 317-323, vol. 29.

Ding, P., et al., "Interfacial Tension in Phase-Separated GelatinfDextran Aqueous Mixtures," *Journal of Colloid and Interface Science*, 2002, pp. 367-376, vol. 253, Elsevier Science USA.

Doukas, J., et al., "Delivery of Fgf Genes to Wound Repair Cells Enhances Arteriogenesis and Myogenesis in Skeletal Muscle," *Molecular Therapy*, 2002, pp, 517-527, vol. 5(5), The American Society of Gene Therapy.

Draye, J.P., et al., "In vitro Release Characteristics of Bioactive Molecules from Dextran Dialdehyde Cross-Linked Gelatin Hydrogel Films," *Biomaterials*, 1998, pp. 99-107, vol. 19, Elsevier Science Ltd.

Draye, J.P., et al., "In vitro and In vivo Biocompatibility of Dextran Dialdehyde Cross-Linked Gelatin Hydrogel Films," *Biomaterials*, 1998, pp. 1677-1687, vol. 19, Elsevier Science Ltd.

Dumitriu, S. and Chornet, E., "Inclusion and Release of Proteins from Polysaccharide-Based Polyion Complexes," *Advanced Drug Delivery Reviews*, 1998, pp. 223-246, vol. 31.

Duncan, A., et al., "Preparation and Characterization of a Poly (2-hydroxyethyl methacrylate) Biomedical Hydrogel," *European Polymer Journal*, 2001, pp. 1821-1826, vol. 37, Elsevier Science Ltd.

Eckert, A., et al., "Surface-Modification of Polystyrene-Microtitre Plates Via Grafting of Glycidylmethactylate and Coating of Poly-Glycidylmethacrylate," *Biomaterials*, 2000, pp. 441-447, vol. 21, Elsevier Science Ltd.

Edelman, M. and Van Der Linden, E., "Compatability of Gelatin and Dextran in Aqueous Solution," *Biomacromolecules*, 2001, pp. 1148-1154, vol. 2(4), American Chemical Society.

Edwards, G., et al., "In vivo Evaluation of a Collagenous Membrane as an Absorbable Adhesion Barrier," *Journal of Biomedical Materials Research*, 1997, pp. 291-297, vol. 34, John Wiley & Sons, Inc.

Einerson, N., et al., "Synthesis and Physiochemical Analysis of Gelatin-Based Hydrogels for Drug Carrier Matrices," *Biomaterials*, 2002, pp. 509-523, vol. 24, Elsevier Science Ltd.

(56) References Cited

OTHER PUBLICATIONS

Englebretsen, Dr, and Harding D.R., "High Yield, Directed Immobilization of a Peptide-Ligand onto a Beaded Cellulose Support," 1994, *Peptide Research*, pp. 322-326, vol. 7(6).
Esposito, E., et al., "Gelatin Microspheres: Influence of Preparation Parameters and Thermal Treatment on Chemico-Physical and Biopharmaceutical Properties," *Biomaterials*, 1996, pp. 2009-2020, vol. 17(20), Elsevier Science Limited, Great Britain.
Fan, H. and Dash, A.K,, "Effect of Cross-Linking on the in vitro Release Kinetics of Doxorubicin from Gelatin Implants," *Int. J. Pharma.*, 2001, pp. 103-116, vol. 213.
Franssen, O. and Hennink, W., "A Novel Preparation Method for Polymeric Microparticles without the Use of Organic Solvents," *Int. J. Pharma.*, 1998, pp. 1-7, vol. 168, Elsevier Science B.V.
Freyman, T., et al., "Fibroblast Contraction of a Collagen-Gag Matrix," *Biomaterials*, 2001, pp. 2883-2891, vol. 22.
Freyman, T., et al., "Micromechanics of Fibroblast Contraction of a Collagen-Gag Matrix," *Experimental Cell Research*, 2001, pp. 140-153, vol. 269, Academic Press.
Friess, W., et al., "Insoluble Collagen Matrices for Prolonged Delivery of Proteins," *Pharm Dev. Technol.*, 1996, pp. 185-193, vol. 1(2).
Fujimori, E., "Cross-Linking and Fluorescence Changes of Collagen by Glycation and Oxidation," *Biochim Biophys Acta*, 1989, pp. 105-110, vol. 998.
Gekko, K, and Fukamizu, M., "Effect of Pressure on the Sol-Gel Transition of Gelatin," *Int. J. Biol. Macromol.*, 1991, pp. 295-300, vol. 13.
Gérentes, P., et al., "Study of a Chitin-Based Gel as Injectable Material in Periodontal Surgery," *Biomaterials*, 2002, pp. 1295-1302, vol. 23, Elsevier Science Ltd.
Gregorius, K. and Theisen, M., "In Situ Deprotection: A Method for Covalent Immobilization of Peptides with Well-Defined Orientation for Use in Solid Phase Immunoassays Such As Enzyme-Linked Immunosorbent Assay," *Analytical Biochemistry*, 2001, pp. 84-91, vol. 299, Academic Press.
Griffon, D., "Evaluation of Osteoproductive Biomaterials: Allograft, Bone Inducing Agent, Bioactive Glass, and Ceramics," Academic Dissertation, Sep, 6, 2002, Dept. of Clinical Veterinary Sciences, University of Helsinki, Finland.
Hansbrough, J,F,, et al., "Burn Wound Closure with Cultured Autologous Keratinocytes and Fibroblasts Attached to a Collagen-Glycoasminoglycan Substrate," *JAMA*, 1989, pp. 2125-2130, vol. 262.
Harding, J. J., "The Unusual Links and Cross-Links of Collagen," *Adv. Protein Chem.*, 1965, pp. 109-190, vol. 20.
Heath, D., et al., "Involvement of Tissue Transglutaminase in the Stabilisation of Biomaterial/Tissue Interfaces Important in Medical Devices," *Biomaterials*, 2002, pp. 1519-1526, vol. 23, Elsevier Science Ltd.
Heiduschka, P. and Thanos, S., "Implantable Bioelectronic Interfaces for Lost Nerve Functions," *Progress in Neurobiology*, 1998, pp. 433-461, vol. 55.
Heijmen, F.H., et al., "Cross-Linking of Dermal Sheep Collagen with Tannic Acid," *Biomaterials*, 1997, pp. 749-754, vol. 18.
Holmes, T., "Novel Peptide-Based Biomaterial Scaffolds for Tissue Engineering," *Trends in Biotechnology*, 2002, pp. 16-21, vol. 20 (1), Elsevier Science, Ltd.
Hong, S., et al., "Study on Gelatin-Containing Artificial Skin IV: A Comparative Study on the Effect of Antibiotic and EGF on Cell Proliferation During Epidermal Healing," *Biomaterials*, 2001, pp. 2777-2783, vol. 22, Elsevier Science Ltd., United Kingdom.
Hörmann, H. et al., "Immobilization of Soluble Fibrin on Fact or Xlla-Coated Polystyrene Beads Mediated by N-Terminal Fibronectin Fragments. II. Demonstration of Covalent Adducts of Fibrin Peptide Chains and Fibronectin Fragments," *Biol. Chem. Hoppe Seyler*, 1991, pp. 427-430, vol. 372.
Huh, K., et al., "Synthesis and Characterization of Dextran Grafted with Poly(*N*-isopropylacrylamide- co-*N*,*N*-dimethyl-acrylamide)," *Macromol. Chem. Phys.*, 2000, pp. 613-619, vol. 201.

Hutmacher, D., "Scaffolds in Tissue Engineering Bone and Cartilage," *Biomaterials*, 2000, pp. 2529-2543, vol. 21, Elsevier Science Ltd.
Iooss, P., etal., "A New Injectable Bone Substitute Combining poly(c-caprolactone) Microparticles with Biphasic Calcium Phosphate Granules," *Biomaterials*, 2001, pp. 2785-2794, vol. 22, Elsevier Science Ltd.
Isgrove, F., et al., "Enzyme Immobilization on Nylon-Optimization and the Steps Used to Prevent Enzyme Leakage from the Support," *Enzyme and Microbial Technology*, 2001, pp. 225-232, vol. 28, Elsevier Science Inc.
Ito, Y., "Micropattern Immobilization of Polysaccharide," *Journal of Inorganic Biochemistry*, 2000, pp. 77-81, vol. 79, Elsevier Science Inc.
Ito, Y., et al., "Artificial Juxtacrine Stimulation for Tissue Engineering," *J. Biomater, Sci. Polymer Edn*, 1998, pp. 879-889, vol. 9(8).
Jansson, K., et al., "A Biodegradable Collagen Membrane as a Dermal Template for Human in vivo Wound Healing," *Scand. J. Plast. Reconstr. Hand Surg.*, 2001, pp. 369-375, vol. 35.
Johnson, R.E., et al., "Thermodynamics of Protein Cross-Links," *Biochemistry*, 1978, pp. 1479-1484, vol. 17(8).
Kaeselev, B., et al., "Photoinduced Grafting of Ultrafiltration Membranes: Comparison of poly(ether sulfone) and poly(sulfone)," *Journal of Membrane Science*, 2001, pp. 245-261, vol. 194, Elsevier Science B.V.
Kam, L., et al., "Selective Adhesion of Astrocytes to Surfaces Modified with Immobilized Peptides," *Biomaterials*, 2002, pp. 511-515, vol. 23, Elsevier Science Ltd.
Kao, W. and Lee, D., "In vivo Modulation of Host Response and Macrophage Behavior by Polymer Networks Grafted with Fibronectin-Derived Biomimetic Oligopeptides: The Role RGD and PHSRN Domains," *Biomaterials*, 2001, pp. 2901-2909, vol. 22, Elsevier Science Ltd.
Kao, W., etal., "Preparation of Heterodifunetional Polyethyleneglycols: Network Formation, Characterization, and Cell Culture Analysis," *J. Biornater. Sci. Polymer Edn*, 2001, pp. 599-611, vol. 12.
Kawai, K., et al., "Accelerated Tissue Regeneration through Incorporation of Basic Fibroblast Growth Factor-Impregnated Gelatin Microspheres into Artificial Dermis," *Biomaterials*, 2000, pp. 489-499, vol. 21, Elsevier Science Ltd.
Kim, C.J. and Lee, P.I., "Composite poly (vinyl alcohol) Beads for Controlled Drug Delivery," *Pharm. Res.*, 1992, pp. 10-16, vol. 9(1).
Kim, Y.J., et al., "Surface Characterization and in vitro Blood Compatibility of poly(ethylene terephthalate) Immobilized with Insulin and/or Heparin Using Plasma Glow Discharge," *Biomaterials*, 2000, pp. 121-130, vol. 21.
König, U., et al, "Durable Surface Modification of poly(tetrafluoroethylene) by Low Pressure H2O Plasma Treatment Followed by Acrylic Acid Graft Polymerization," *Colloids and Surfaces B: Biointerfaces*, 2002, pp. 63-71, vol. 24, Elsevier Science B.V.
Koob, T. and Hernandez, D., Material Properties of Polymerized NDGA-Collagen Composite Fibers: Development of Biologically Based Tendon Constructs, *Biomaterials*, 2002, pp. 203-212, vol. 23, Elsevier Science Ltd.
Korrt, a., et al., "Nonspecific Amine Immobilization of Ligand Can Be a Potential Source of Error in BIAcore Binding Experiments and May Reduce Binding Affinities," *Anal. Biochem.*, 1997, pp. 103-111, vol. 253.
Kosmala, J., et al., "Preparation of Interpenetrating Networks of Gelatin and Dextran as Degradable Biomaterials," *Biomaterials*, 2000, pp. 2019-2023, vol. 21, Elsevier Science Ltd.
Kröger, D., et al., "Immobilization of Histidine-Tagged Proteins on Gold Surfaces Using Chelator Thioalkanes," *Biosens. Bioelectron.*, 1999, pp. 155-161, vol. 14.
Kuijpers, A.J., et al., "Controlled Delivery of Antibacterial Proteins from Biodegradable Matrices," *J. Control Release*, 1998, pp. 235-247, vol. 53.
Kuijpers, A.J., et al., "Cross-Linking and Characterizations of Gelatin Matrices for Biomedical Applications," *J. Biomater Sci Polym Ed.*, 2000, pp. 225-243, vol. 11.

(56) References Cited

OTHER PUBLICATIONS

Kuijpers, A.J., et al ., "In vitro and in vivo Evaluation of Gelatin-Chondroitin Sulphate Hydrogels for Controlled Release of Antibacterial Proteins," *Biomaterials*, 2000, pp, 1763-1772, vol. 21.

Kuijpers, A.J., et al., In vivo and in vitro Release of Lysozyme from Cross-Linked Gelatin Hydrogels: a Model System for the Delivery of Antibacterial Proteins from Prosthetic Heart Valves, *J. Control Release*, 2000, pp. 323-336, vol. 67.

Kuijpers, A.J., et al., "In vivo Compatability and Degradation of Crosslinked Gelatin Gels Incorporated in Knitted Dacron," *J. Biomed Mater Res.*, 2000, pp. 136-145, vol. 51.

Kurisawa, M. and Yui, N., "Gelatin/Dextran Intelligent Hydrogels for Drug Delivery: Dual- Stimuli-Responsive Degradation in Relation to Miscibility in Interpenetrating Polymer Networks," *Macromol. Chem. Phys.*, 1998, pp. 1547-1554, vol. 199, Wiley-VCH Verlag GmbH, D-69451, Weinheim.

Kuzuya, M., et al., "Glycation Cross-Links Inhibit Matrix Metalloproteinase-2 Activation in Vascular Smooth Muscle Cells Cultured on Collagen Lattice," *Diabetologia*, 2001, pp. 433-436, vol. 44.

Lando, D.Y., Melting of Cross-Linked DNA: I. Model and Theoretical Methods, *J. Biomol. Struct. Dyn.*, 1997, pp. 129-140, vol. 15(1).

Larm, O., etal., "A New Non-Thrombogenic Surface Prepared by Selective Covalent Binding of Heparin via a Modified Reducing Terminal Residue," *Biomat. Med. Dev. Artif. Organs*, 1983, pp. 161-173, vol. 11.

Lebaron, R.G., et al., "Extracellular Matrix Cell Adhesion Peptides: Functional Applications in Orthopedic Materials," *Tissue Eng.*, 2000, pp. 85-103, vol. 6(2).

Lee, J.M., et al., "Crosslinking of Tissue-Derived Biomaterials in 1-ethy1-3(3-dimethylaminopropyl)-carbodiimide (EDC)," *J. Mater. Sci. Mat. Med.*, 1996, pp. 531-541, vol. 7.

Lii, C., et al., "Carboxymethyl Cellulose-Gelatin Complexes," *Carbohydrate Polymers*, 2002, pp. 19-26, vol. 50, Elsevier Science Ltd.

Lii, C., et al., "Xanthan Gum-Gelatin Complexes," *European Polymer Journal*, 2002, pp. 1377-1381, vol. 38, Elsevier Science Ltd.

Lin, F., et al., "Biological Effects and Cytotoxicity of the Composite Composed by Tricalcium Phosphate and Glutaraldehyde Cross-Linked Gelatin," *Biomaterials*, 1998, pp. 905-917, vol. 19, Elsevier Science Ltd.

Liu, H., et al., "Osteogenic Evaluation of Glutaraldehyde Crosslinked Gelatin Composite with Fetal Rat Calvarial Culture Model, " *Artificial Organs*, 2001, pp. 644-654, vol. 25(8), Blackwell Science, Inc.

Liu, L., et al., "An Osteoconductive Collagen/Hyaluronate Matrix for Bone Regeneration," *Biomaterials*, 1999, pp. 1097-1108, vol. 20, Elsevier Science Ltd.

Ljungquist, C., et at, "Thiol-Directed Immobilization of Recombinant IgG-Binding Receptors," *Eur. J. Biochem.*, 1989, pp. 557-561, vol. 186.

Lou, X. and Chirila, T.V., "Swelling Behavior and Mechanical Properties of Chemically Cross- Linked Gelatin Gels for Biomedical Use," *J. Biomater. Appl.*, 1999, pp. 184-91, vol. 14(2).

Ma, X., et al., "Thermal Cross-Linking for Biologically Degradable Materials," *ASAIO J.*, Preliminary Report, 1996, pp. M866-M871, vol. 42(5).

Madhan, B., et al., "Study on the Stabilization of Collagen with Vegetable Tannins in the Presence of Acrylic Polymer," *Biomaterials*, 2002, pp. 2841-2847, vol. 23(14).

Marois, Y,, et al., "Carbomiimide Cross-Linked Gelatin: A New Coating for Porous Polyester Arterial Prostheses," *Biomaterials*, 1995, pp. 1131-1139, vol. 16.

Massia, S. and Hubbell, J., "Covalent Surface Immobilization of Arg-Gly-Asp- and Tyr-Ile-Gly-Ser-Arg-Containing Peptides to Obtain Well-Defined Cell-Adhesive Substrates," *Analytical Biochemistry*, 1990, pp. 292-301, vol. 187, Academic Press, Inc.

Massia, S. and Stark, J., "Immobilized Rgd Peptides on Surface-Grafted Dextran Promote Biospecific Cell Attachment," *J. Biomed. Mater. Res.*, 2001, pp. 390-399, vol. 56, John Wiley & Sons, Inc.

Massia, S., et al., "Surface-Immobilized Dextran Limits Cell Adhesion and Spreading," *Biomaterials*, 2000, pp, 2253-2261, vol. 21, Elsevier Science Ltd.

Matsuda, T. and Magoshi, T., "Preparation of Vinylated Polysaccharides and Photofabrication of Tubular Scaffolds as Potential Use in Tissue Engineering," *Biomacromolecules*, 2002, pp. 942-950, vol. 3, American Chemical Society.

Mentink, C., et at, "Glucose-Mediated Cross-Linking of Collagen in Rat Tendon and Skin," *Clinica Chitnica Acta*, 2002, pp. 69-76, vol. 321, Elsevier Science B.V.

Mo, X., et al., "Soft Tissue Adhesive Composed of Modified Gelatin and Polysaccharides," *J. Biomater. Sci*, Polymer Edn., 2000, pp. 341-351, vol. 11(4), VSP 2000.

Murray, F. and Hutton, P,, "Gelling of Urea-Linked Gelatin with Fresh Frozen Plasma," *Anaesthesia*, 1989, pp. 392-393, vol. 44(5).

Naftalin, R.J. and Symonds, M,C., "The Mechanisms of Sugar-Dependent Stabilisation of Gelatin Gels," *Biochim. Biophys. Acta*, 1974, pp. 173-178, vol. 352.

Navarro, F., etal., "Sprayed Keratinocyte Suspensions Accelerate Epidermal Coverage in a Porcine Microwound Model," *J. Burn Care Rehabil.*, 2000, pp. 513-518, vol. 21.

Nguyen, Q., et al., "Simple Method for Immobilization of Bio-Macromolecules onto Membranes of Different Types," *Journal of Membrane Science*, 2002, pp. 1-11, vol. 5494, Elsevier Science B.V.

Nouaimi, M., et al., "Immobilization of Trypsin on Polyester Fleece via Different Spacers," *Enzyme and Microbial Technology*, 2001, pp, 567-574, vol. 29.

Nouvel, C., et al., "Partial or Total Silylation of Dextran with Hexamethyldislazane," *Polymer*, 2002, pp. 1735-1743, vol. 43, Elsevier Science Ltd.

Olbrich, K., et al., "Surfaces Modified with Covalently-Immobilized Adhesive Peptides Affect Fibroblast Population Motility," *Biomaterials*, 1996, pp. 759-764, vol. 17, Elsevier Science Limited.

Olde Damink, L., et al., "Crosslinking of Dermal Sheep Collagen Using Hexamethylene Diisocyanate," *J. Mater. Sci. Mat. Med.*, 1995, pp. 429-434, vol. 6.

Olde Damink, L., et al., "Cross-Linking of Dermal Sheep Collagen Using a Water Soluble Carbodiimide," *Biomaterials*, 1996, pp. 765-773, vol. 17(8).

Olde Damink, L., et al., "Glutaraldehyde as a Crosslinking Agent for Collagen-Based Biomaterials," *J. Mater. Sci. Mat. Med.*, 1995, pp, 460-472, vol. 6.

Otani, Y. et al., Effect of Additives on Gelation and Tissue Adhesion of Gelatin-poly(L-glutamic acid) Mixture, *Biomaterials*, 1998, pp. 2167-2173, vol. 19.

Pankaj, M., "Vaccine Delivery System for Immunization, Using Biodegradable Polymer Microspheres," *PatentsALERT*, U.S. Pat. No. 5,569,468.

Park, S., et al., "Characterization of Porous Collagen/Hyaluronic Acid Scaffold Modified by 1-ethyl-3-(3-dimethylaminopropyl)carbodiimide Cross-Linking," *Biomaterials*, 2002, pp. 1205-1212, vol. 23, Elsevier Science Ltd.

Pierce Technical Handbook, 1994, Pierce Biotechnology, Inc. (available on-line@www.piercenet.com).

Piez, K.A., "Chemistry of Collagen and Its Cross-Links," *Isr. J. Med. Sci.*, 1971, p. 453, vol. 7(3).

Puleo, D.A., et al,, "A Technique to Immobilize Bioactive Proteins, Including Bone Morphogenetic Protein-4 (BMP-4), on Titanium Alloy," *Biomaterials*, 2002, pp. 2079-2087, vol. 23, Elsevier Science Ltd.

Rao, J.K., et al., "Controlled Release Systems for Proteins Based on Gelatin Microspheres," *J. Biomater. Sci. Polym. Ed.*, 1994, pp, 391-398, 1994, vol. 6(5).

Ratner, B., "Reducing Capsular Thickness and Enhancing Angiogenesis Around Implant Drug Release Systems," *J Control. Release*, 2002, pp. 211-218, vol. 78, Elsevier Science B.V.

Ravin, A., et al., "Long-and Short-Term Effects of Biological Hydrogels on Capsule Microvascular Density Around Implants in Rats," *Journal of Biomedical Material Resources (Applied Biotnaterials)*, 2001, pp. 313-318, vol. 58, John Wiley & Sons, Inc.

(56) References Cited

OTHER PUBLICATIONS

Rosa, C., et al., "Optical Biosensor Based on Nitrite Reductase Immobilized in Controlled Pore Glass," *Biosen Bioelec.*, 2002, pp. 45-52, vol. 17.
Ruys, L., et al., "Polymer Drug Combinations. VII. Polymethacrylates and Modified Polysaccharides with Potential Antianhythmic Activity," *Acta Pharmaceutica Technologica*, 1983, pp. 105-112, vol. 29(2).
Sajitiilal, G., et al., "Advanced Glycation End Products Induce Crosslinking of Collagen in vitro," *Biochimica et Biophysica Acta*, 1998, pp. 215-224, vol. 1407, Elsevier Science B.V.
Sakiyama, S.E., etal., "Incorporation of Heparin-Binding Peptides into Fibrin Gels Enhances Neurite Extension: an Example of Designer Matrices in Tissue Engineering," *FASEB J.*, 1999, pp. 2214-2224, vol. 13(15).
Schacht, E., et al., "Hydrogels Prepared by Crosslinking of Gelatin with Dextran Dialdehyde," *Reactive & Functional Polymers*, 1997, pp. 109-116, vol. 33, Elsevier Science B.V.
Scholten, E., et al., "Interfacial Tension of a Decomposed Biopolymer Mixture," *Langmuir*, 2002, pp. 2234-2238, vol. 18(6), American Chemical Society.
Sershen, S. and West, J., "Implantable, Polymeric Systems for Modulated Drug Delivery," *Advanced Drug Delivery Reviews*, 2002, pp. 1225-1235, vol. 54, Elsevier Science B,V,.
Sheehan, J.C. and Hlavka, J.J., "The Crosslinking of Gelatin Using a Water-Soluble Carbomiimide," *J. Am. Chem. Soc.*, pp. 4528-4529, vol. 79.
Shpigel, E., etal., "Immobilization of Recombinant Herparinase I Fused to Cellulose-Binding Domain," *Biotechnol Bioeng.*, Oct. 5, 1999, pp. 17-23, vol. 65(1).
Smeds, K. and Grinstaff, M., "Photocrosslinkable Polysaccharides for In Situ Hydrogel Formation," *J. Biomed. Mater. Res.*, 2001, pp. 115-121, Vol, 54, John Wiley & Sons, Inc.
Speer, D.P, et al., "Biological Effects of Residual Glutaraldehyde in Glutaraldehyde-Tanned Collagen," *J. Biomed. Mater. Res.*, 1980, pp. 753-764, vol. 14.
Strauss, A. and Gotz, F., "In vivo Immobilization of Enzymatically Active Polypeptides on the Cell Surface of *Staphylococcus carnosus*," *Mol. Microbiol.*, 1996, pp. 491-500, vol. 21(3).
Sundholm, F, and Visapaa, A., "Cross-Linking of Collagen in the Presence of Oxidizing Lipid," *Lipids*, 1978, pp. 755-757, vol. 13(11).
Sung, H.W., et al., Crosslinking Characteristics of Biological Tissues Fixed with Monofunctional or Multifunctional Epoxy Compounds, *Biomaterials*, 1996, pp. 1405-1410, vol. 17.
Sutherland, I.W., "Novel and Established Applications of Microbial Polysaccharides," *TIBTECH*, 1998, pp. 41-46, vol. 16.
Tabata, Y. and Ikada, Y., "Vascularization Effect of Basic Fibroblast Growth Factor Released from Gelatin Hydrogels with Different Biodegradabilities," *Biomaterials*, 1999, pp. 2169-2175, vol. 20, Elsevier Science Ltd.
Tromp, R., et al., "Confocal Scanning Light Microscopy (CSLM) on Mixtures of Gelatin and Polysaccharides," *Food Research International*, 2001, pp, 931-938, vol. 34, Elsevier Science Ltd.
Tsai, C., et al., "Effects of Heparin Immobilization on the Surface Characteristics of a Biological Tissue Fixed with a Naturally Occurring Crosslinking Agent (GENIPIN): an in vitro Study," *Biomaterials*, 2001, pp. 523-533, Vol, 22, Elsevier Science Ltd.
Ulubayram, K., et al., "EGF Containing Gelatin-Based Wound Dressings," *Biomaterials*, 2001, pp. 1345-1356, vol. 22.
Vandelli, M.A., et al., "The Concentration of the Cross-Linking Agent as a Tool for the Control of Release and Swelling Properties of Gelatin Microspheres," *J. Pharm. Belg.*, 1991, pp. 381-388, vol. 46.
Vandelli, M.A., et al., "The Effect of the Cross-Linking Time Period Upon the Drug Release and the Dynamic Swelling of Gelatin Microspheres," *Pharmazie*, 1991, pp. 866-869, vol. 46(12).
Van Wachem, P., et al., "(Electron) Microscopic Observations on Tissue Integration of Collagen-Immobilized Polyurethane," *Biomaterials*, 2002, pp. 1401-1409, vol. 23, Elsevier Science Ltd.
Van Wachem, P., et al., "In vivo Biocompatibility of Carbodiimide-Crosslinked Collagen Matrices: Effects of Crosslink Density, Heparin Immobilization, and bFGF Loading," *J. Biomed. Mater. Res.*, 2001, pp. 368-378, vol. 55(3).
Vaz, C., et al., "Use of Coupling Agents to Enhance the Interfacial Interactions in Starch-EVOH/Hydroxylapatite Composites," *Biomaterials*, 2002, pp. 629-635, vol. 23, Elsevier Science Ltd.
Walton, D., et al., "Electrosynthetic Modification of Proteins: Electrooxidations at Methionine and Tryptophan in Hen Egg-White Lysozyme," *Electrochimica Acta*, 1997, pp. 2285-2294, vol. 42(15), Elsevier Science Ltd., Great Britain.
Wang, J., et al., "One-Step Electropolymeric Co-Immobilization of Glucose Oxidase and Heparin for Amperometric Biosensing of Glucose," *Analyst*, 2000, pp. 1431-1434, vol. 125.
Weadock, K., et al., "Evaluation of Collagen Crosslinking Techniques," *Biomat. Med. Dev. Art Org.*, 1983, pp. 293-318, vol. 11.
Welz, M.M. and Ofner, C.M., "Examination of Self-Crosslinked Gelatin as a Hydrogel for Controlled Release," *J. Pharm, Sci.*, 1992, pp. 85-90, vol. 81(1).
Wissink, M., et al., "Binding and Release of Basic Fibroblast Growth Factor from Heparinized Collagen Matrices," *Biomaterials*, 2001, pp. 2291-2299, vol. 22, Elsevier Science Ltd.
Wissink, M., et al., "Immobilization of Heparin to EDC/NHS-Crosslinked Collagen, Characterization and in vitro Evaluation," *Biomaterials*, 2001, pp. 151-163, vol. 22, Elsevier Science Ltd.
Wissink, Mi, et al., "Improved Endothelialization of Vascular Grafts by Local Release of Growth Factor from Heparinized Collagen Matrices," *J. Control Release*, 2000, pp. 103-114, vol. 64.
Xu, G., et al., "Free Electron Laser Induces Specific Immobilization of Heparin on Polysulfone Films," *Biomater. Sci. Polym. Ed.*, 2001, pp. 503-514, vol. 12(5).
Yannas, I.V. and Tobolsky, a.V., "Cross-Linking of Gelatine by Dehydration," *Nature*, 1967, pp. 509-510, vol. 215(100).
Yaylacalu, M.B., et al., "Development of a Calcium Phosphate-Gelatin Composite as a Bone Substitute and its Use in Drug Release," *Biomaterials*, 1999, pp. 711-719, vol. 20.
Zaleskas, J.M., "Growth Factor Regulation of Smooth Muscle Actin Expression and Contraction of Human Articular Chondrocytes and Meniscal Cells in a Collagen-Gag Matrix," *Exp. Cell Res.*, 2001, pp, 21-31, vol. 270.
Zhao, H. and Heindel, N., "Determination of Degree of Substitution of Fromyl Groups in Polyaldehyde by the Hydroxlamine Hydrochloride Method," *Pharmaceutical Research*, 1991, pp. 400-402, vol. 8(3), Plenum Publishing Corporation.
Zimmermann, J., et al., "Novel Hydrogels as Support for in vitro Cell Growth: poly(ethlene glycol)- and Gelatine-Based (meth)acrylamidopeptide Macromonomers," *Biomaterials*, 2002, pp. 2127-2134, vol. 23, Elsevier Science Ltd.

* cited by examiner

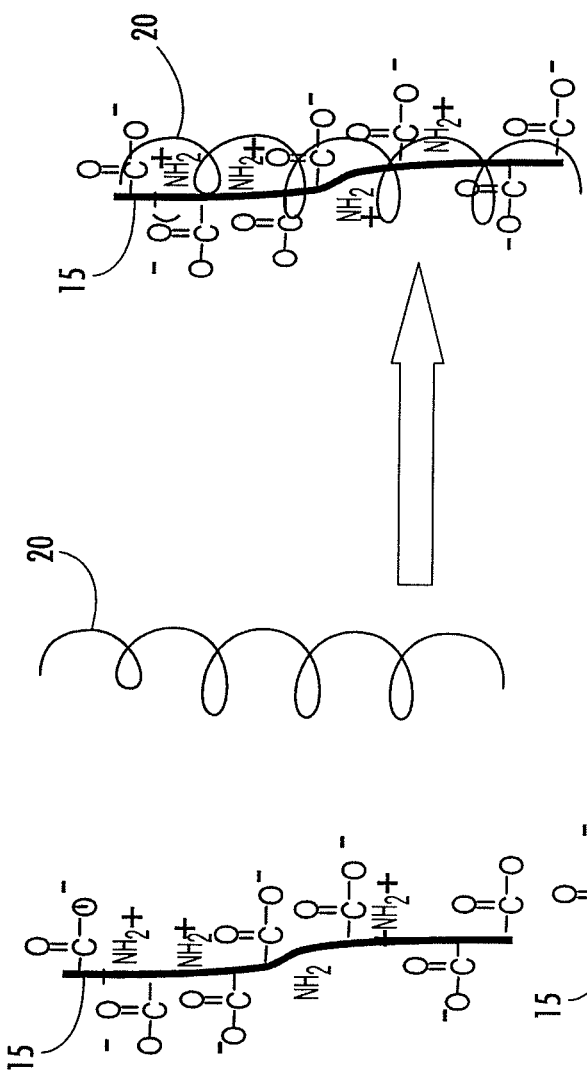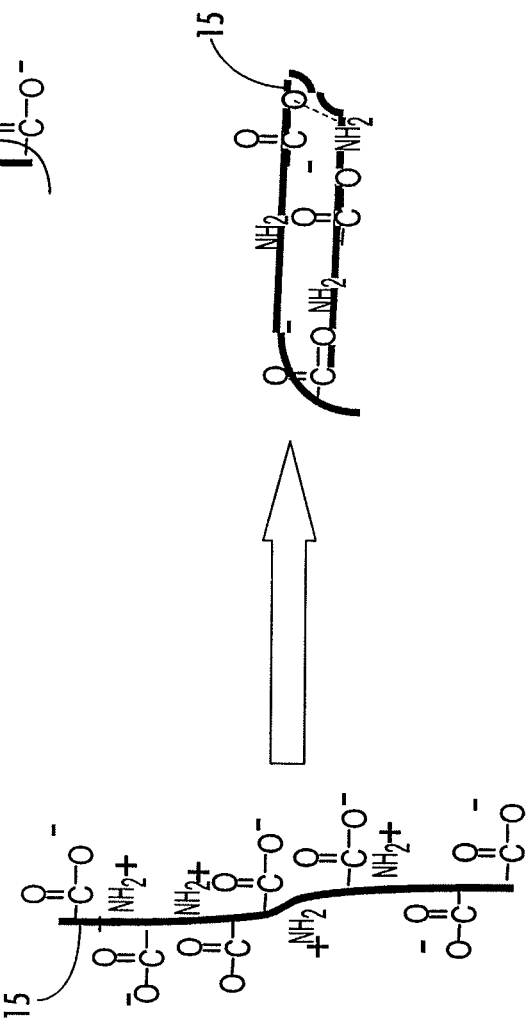

IMMOBILIZED BIOACTIVE HYDROGEL MATRICES AS SURFACE COATINGS

CROSS-REFERENCE TO RELATED APPLICATIONS

This application is a continuation of U.S. patent application Ser. No. 11/937,851, filed Nov. 9, 2007, which is a continuation of U.S. patent application Ser. No. 10/372,757, filed Feb. 21, 2003 (now U.S. Pat. No. 7,303,814), which claims the benefit of priority of Provisional Application Ser. No. 60/358,625, filed Feb. 21, 2002, the disclosures of which are incorporated herein by reference in their entirety.

FIELD OF THE INVENTION

The present invention relates to cross-linked bioactive hydrogel matrices that are appropriate for use as immobilized bioactive coatings to improve the integration and performance of medical devices.

BACKGROUND OF THE INVENTION

The replacement of damaged or diseased tissues or organs by implantation has been, and continues to be, a long-standing goal of medicine towards which tremendous progress has been made. In addition, much progress has also been made in the field of treating patients with medical conditions through the implantation of therapeutic medical devices, such as glucose sensors and pacemakers. However, one of the most serious problems restricting the use of implants is the wound healing response elicited by implanted foreign materials (Ratner, B. D., "Reducing capsular thickness and enhancing angiogenesis around implant drug release systems" *Journal of Controlled Release* 78:211-218 (2002)).

Biocompatibility is defined as the appropriate response of the host to a foreign material used for its intended application. Biocompatibility further refers to the interaction between the foreign material and the tissues and physiological systems of the patient treated with the foreign material. Protein binding and subsequent denaturation as well as cell adhesion and activation have been invoked as determinants of a material's biocompatibility. Biocompatibility also implies that the implant avoids detrimental effects from the host's various protective systems and remains functional for a significant period of time. With respect to medical devices, biocompatibility is determined to a large extent by the type of acute reaction provoked by implantation. The extent to which a medical device is integrated with the surrounding tissue depends upon the type of wound healing response that is evoked by the implanted material. In vitro tests designed to assess cytotoxicity or protein binding are routinely used for the measurement of a material's potential biocompatibility. In other words, the biocompatibility of a material is dependent upon its ability to be fully integrated with the surrounding tissue following implantation.

The modulation of this tissue response to an implanted medical device comprised of a foreign material is pivotal to successful implantation and performance of such medical devices. Mammalian systems recognize foreign materials, such as surgically implanted objects or medical devices. Upon binding to sites on these foreign materials, a cascade of events occur that notify inflammatory cells to surround such materials and initiate a series of wound healing events which ultimately lead to the formation of an avascular fibrous capsule surrounding the implanted device. The formation of an avascular fibrous capsule can severely limit the life and usefulness of the implanted medical device, especially in situations where direct contact with specific tissue, such as vascular tissue, muscle tissue, or nerve tissue is vital to the effectiveness of the device.

Previous research has shown that the specific interactions between cells and their surrounding extracellular matrix play an important role in the promotion and regulation of cellular repair and replacement processes (Hynes, S. O., "Integrins: a family of cell surface receptors" *Cell* 48:549-554 (1987)). Consequently, there has been a heightened interest in work related to biocompatible polymers useful in therapeutic applications. One particular class of polymers that have proven useful for such applications, including contact lens materials, artificial tendons, matrices for tissue engineering, and drug delivery systems, is hydrogels (Wheeler J C, Woods J A, Cox M J, Cantrell R W, Watkins F H, Edlich R F.; Evolution of hydrogel polymers as contact lenses, surface coatings, dressings, and drug delivery systems.; J Long Term Eff Med Implants. 1996; 6(3-4):207-17 and Schacht, E., "Hydrogels prepared by crosslinking of gelatin with dextran dialdehyde" *Reactive & Functional Polymers* 33:109-116 (1997)). Hydrogels are commonly accepted to be materials consisting of a permanent, three-dimensional network of hydrophilic polymers with water filling the space between the polymer chains, and they may be obtained by copolymerizing suitable hydrophilic monomers, by chain extension, and by cross-linking hydrophilic pre-polymers or polymers.

Prior work has shown that a thermoreversible hydrogel matrix, which is liquid near physiologic temperatures, elicits vasculogenesis and modulates wound healing in dermal ulcers (Usala A L, Dudek R, Lacy S, Olson J, Penland S, Sutton J, Ziats N P, Hill R S: Induction of fetal-like wound repair mechanisms in vivo with a novel matrix scaffolding. Diabetes 50 (Supplement 2): A488 (2001); and Usala A L, Klann R, Bradfield J, Ray S, Hill R S, De La Sierra D, Usala M, Metzger M, Olson G: Rapid Induction of vasculogenesis and wound healing using a novel injectable connective tissue matrix. Diabetes 49 (Supplement 1): A395 (2000)). This bioactive hydrogel material has also been shown to improve the healing in response to implanted foreign materials; demonstrating a decrease in the surrounding fibrous capsule thickness and a persistent increase in blood supply immediately adjacent to implanted materials exposed to this thermoreversible hydrogel (Ravin A G, Olbrich K C, Levin L S, Usala A L, Klitzman B.; Long- and short-term effects of biological hydrogels on capsule microvascular density around implants in rats. J Biomed Mater Res. 2001 May 1; 58(3):313-8.). However the use of such a bioactive thermoreversible hydrogel as a biomaterial coating for a medical device is not practical for devices requiring three-dimensional or thermal stability. Accordingly, there is a need for a bioactive material that is stable at body temperatures and thus appropriate for use as a coating for use with medical devices, particularly those intended for implantation into mammals.

BRIEF SUMMARY OF THE INVENTION

The invention provides a coated substrate, comprising a substrate having a surface, and a bioactive hydrogel matrix layer overlying the surface of the substrate and immobilized thereon, the hydrogel matrix layer comprising a first high molecular weight component and a second high molecular weight component, the first and second high molecular weight components each being selected from the group consisting of polyglycans and polypeptides. As used herein, the term "immobilized" refers to affixation of one or more components of the hydrogel matrix layer via any chemical or mechanical bonding force or process, such as by covalent attachment. The hydrogel matrix coating may further comprise one or more enhancing agents selected from the group consisting of polar amino acids, amino acid analogues, amino acid derivatives, intact collagen, and divalent cation chelators.

Preferred substrates include medical devices. The bioactive hydrogel compositions are useful both as a layer that serves as a structural component of a medical device and as a bioactive hydrogel coating that modulates the wound healing response to an implanted device and improves tissue integration of a medical device. As a structural component of a medical device, bioactive hydrogel-coated biomaterials can be designed as a space-filling scaffold used to direct tissue organization and vascularization of a medical device. One exemplary use would be as a composite wound healing device comprising a polymeric microbial barrier and an immobilized bioactive hydrogel of sufficient thickness to provide a three dimensional structure to fill anatomic voids such as those resulting from donor-site tissue harvesting. As a functional coating of a medical device, bioactive hydrogel coatings are expected to reduce the avascular capsule surrounding an implanted device, and improve the intimate contact between surrounding tissues and active device elements and hence the performance of devices such as implanted glucose sensors for closed-loop control of diabetes. The compositions are also useful as bioactive hydrogel coatings for artificial organs containing functional tissue cells, and other passive or active medical devices or implants, and other biosensors.

Also provided is a method of preparing a coated substrate, such as a coated medical device. The method comprises immobilizing a first high molecular weight component on the surface of the substrate, wherein the first molecular weight component is selected from the group consisting of polyglycans and polypeptides. The first high molecular weight component is contacted with a second high molecular weight component also selected from the group consisting of polyglycans and polypeptides. The contacting step occurs before, during or after the immobilizing step. The two high molecular weight components form an immobilized bioactive hydrogel coating on the surface of the substrate. Preferably, one of the high molecular weight components is a polyglycan, such as dextran, and the other is a polypeptide, such as gelatin.

In a preferred embodiment, the immobilizing step comprises covalently attaching at least one of the high molecular weight components to the surface of the substrate. One or more of the high molecular weight components and/or the surface can be chemically modified, such as by oxidation or amination, to form reactive sites thereon capable of participating in covalent bonding. The high molecular weight components can be modified to comprise a plurality of pendant reactive groups along the backbone of the molecule or a single reactive group located at each terminus thereof.

BRIEF DESCRIPTION OF THE DRAWINGS

Figure 1:
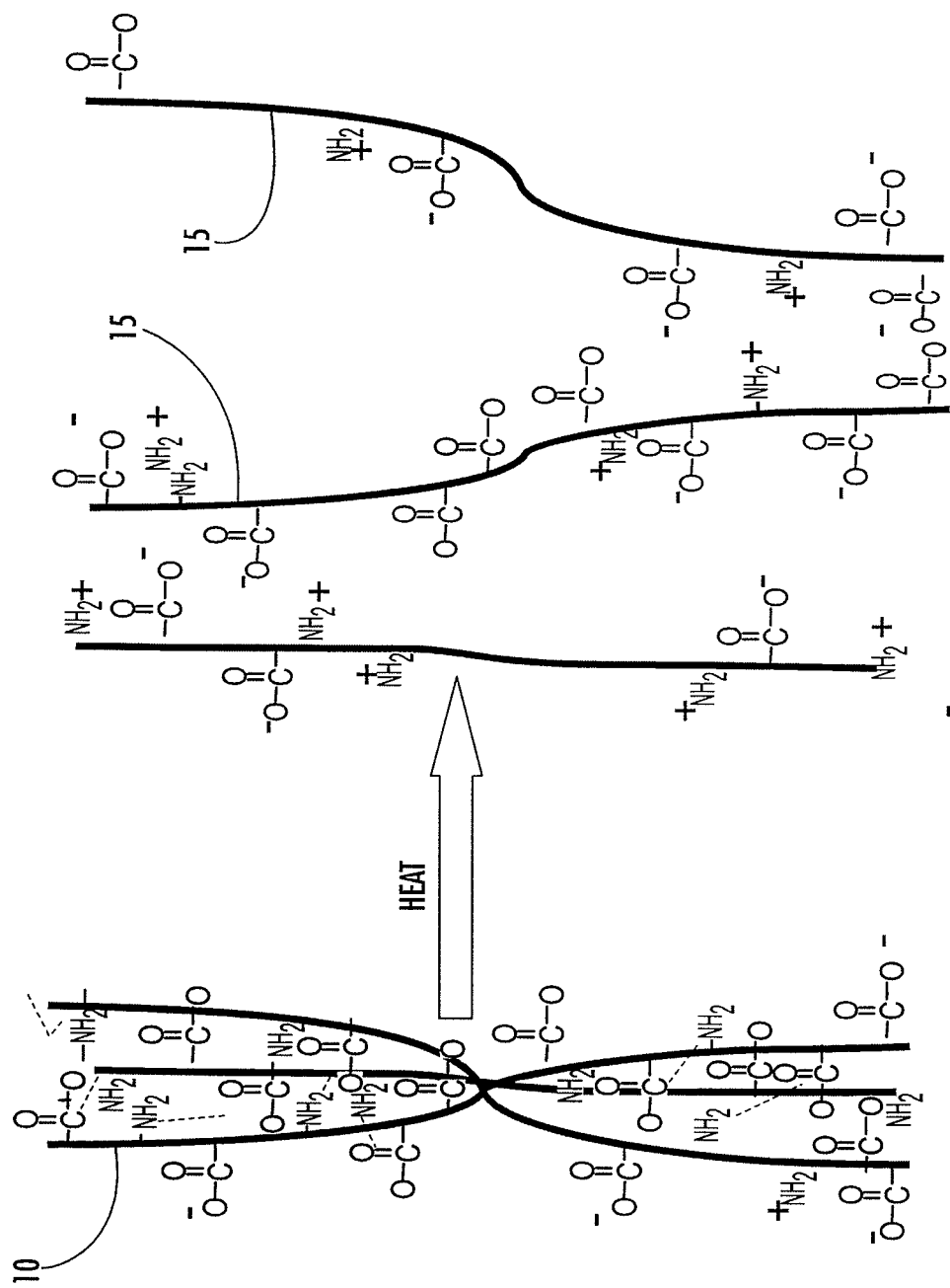
Figure 3:
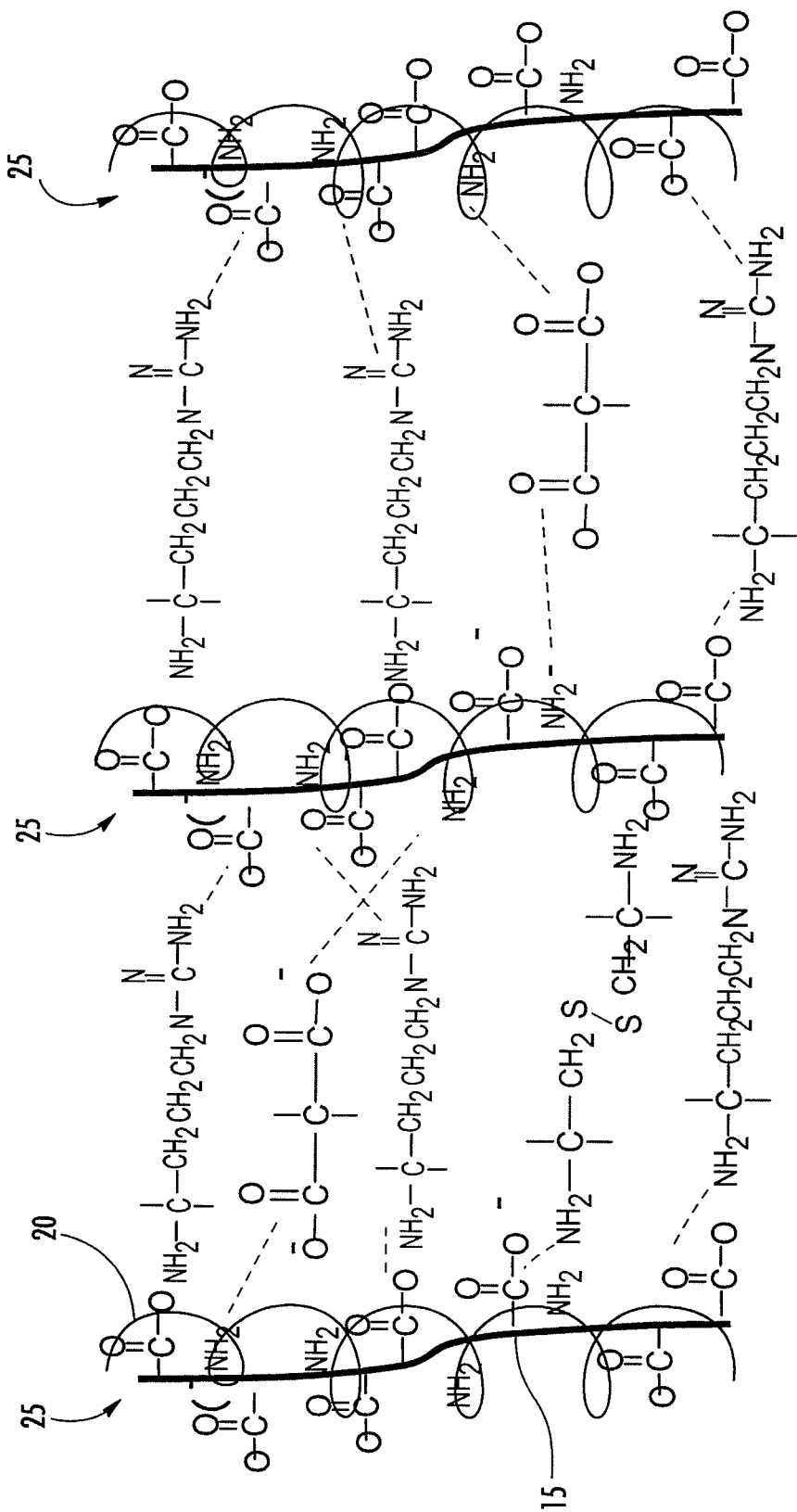
Figure 4B:
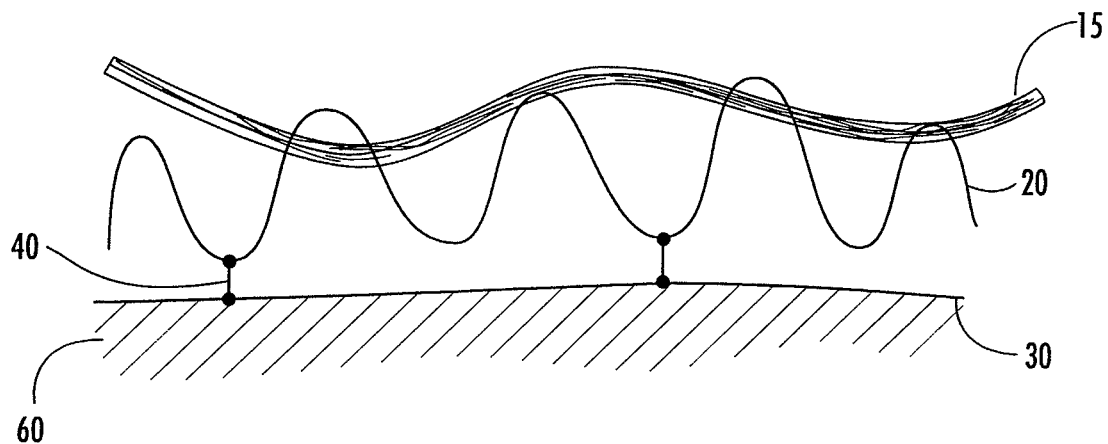
Figure 4A:
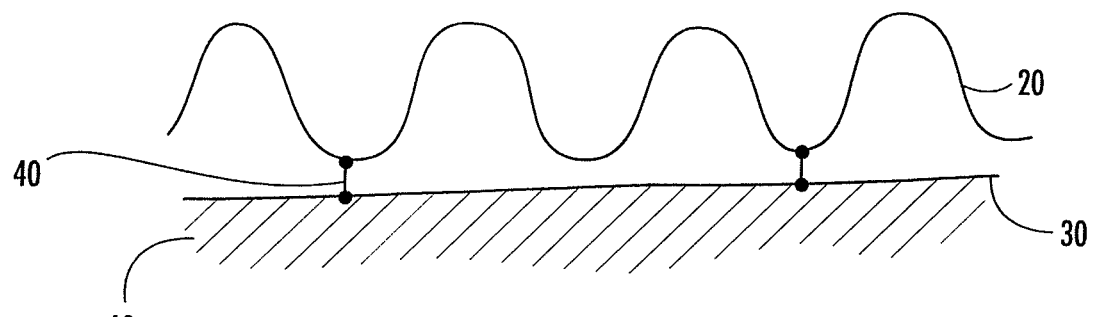
Figure 5:
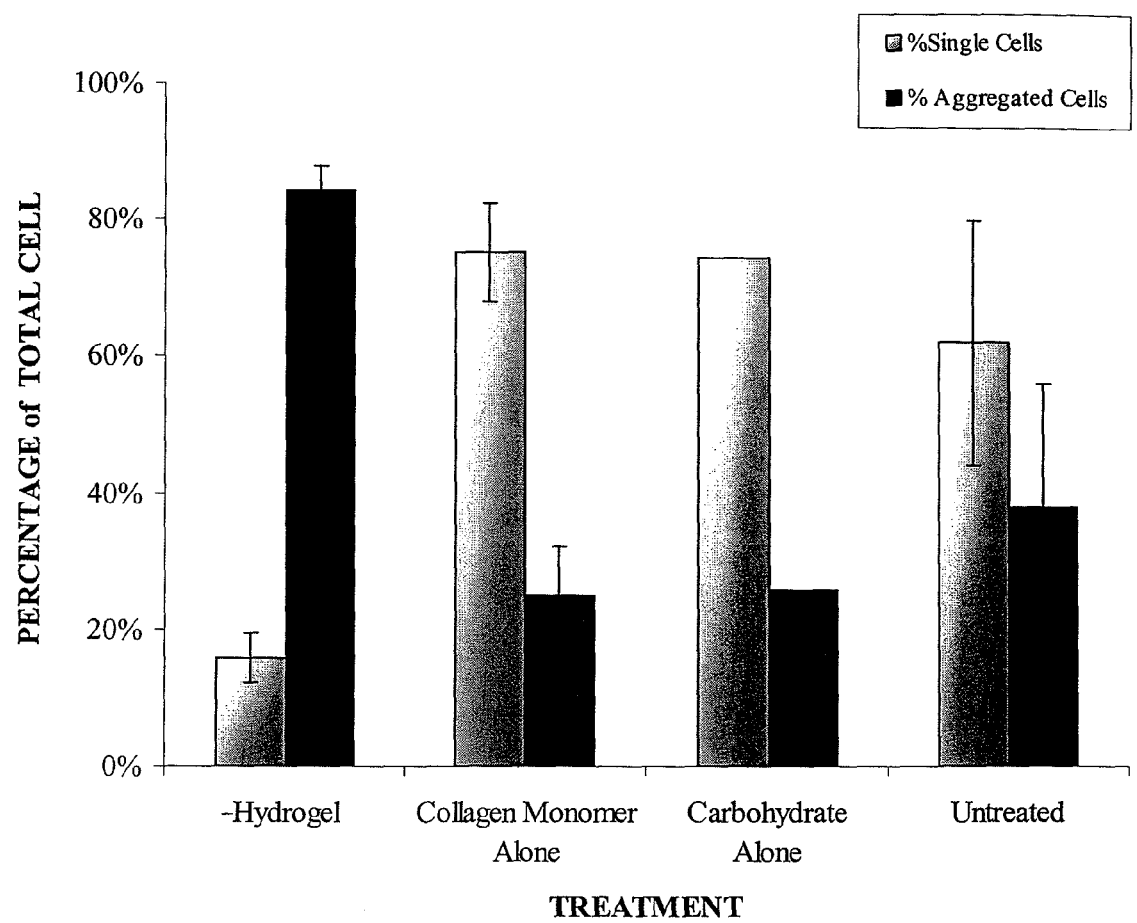
Figure 6:
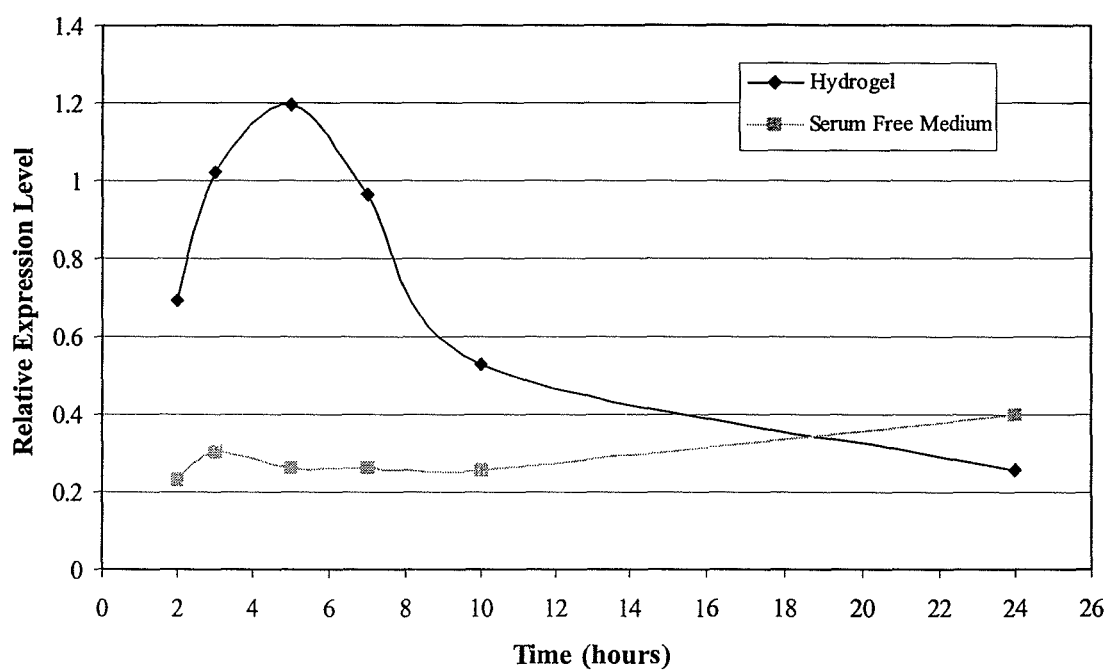
Figure 7:
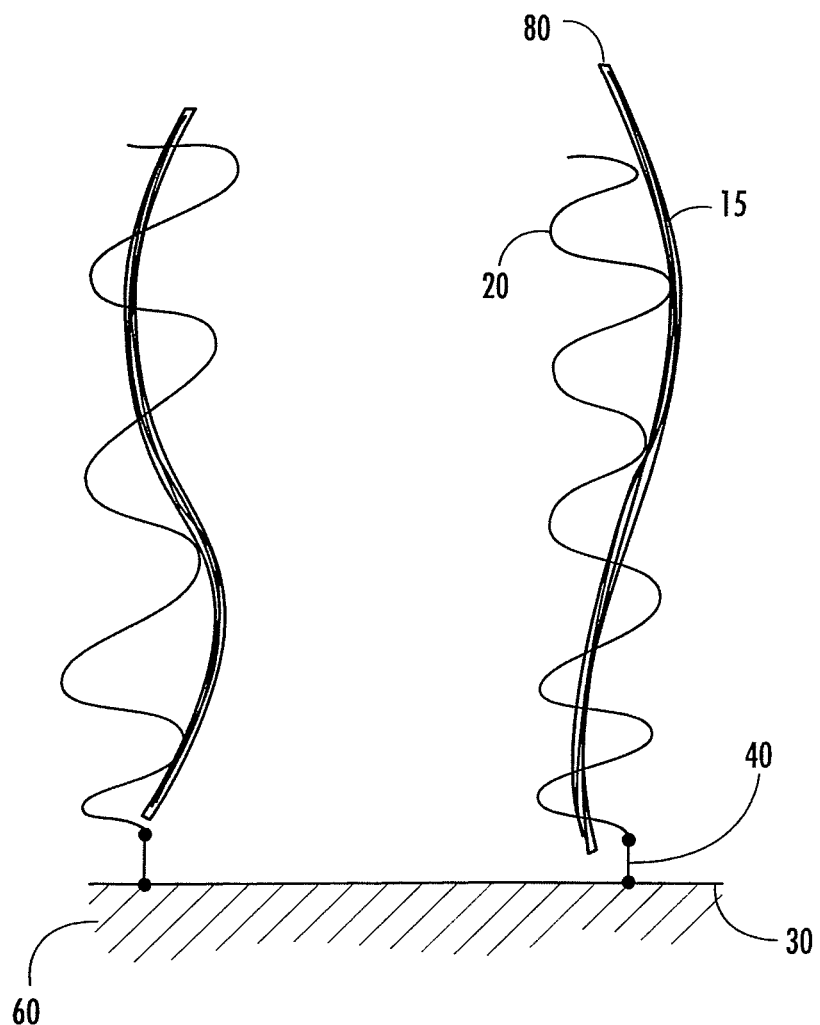
Figure 8:
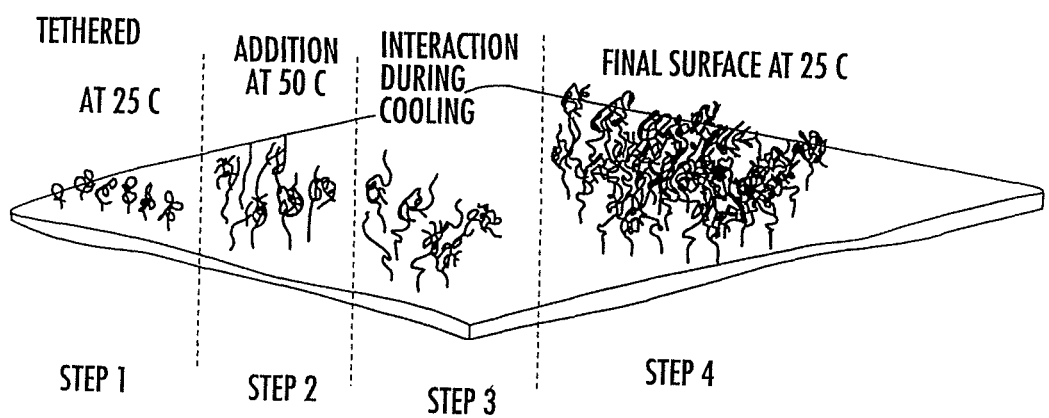
Figure 9:
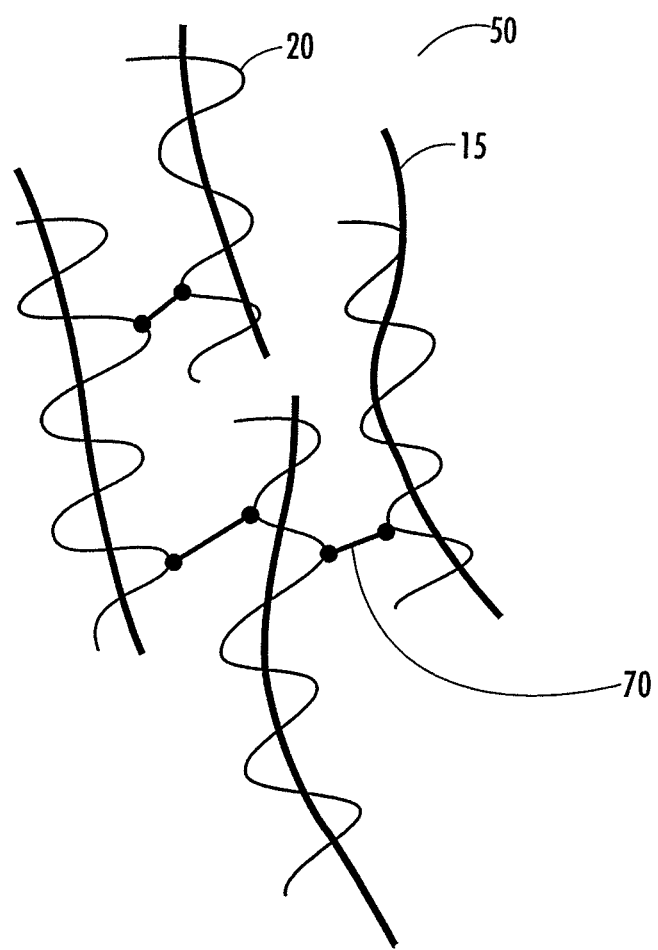

Having thus described the invention in general terms, reference will now be made to the accompanying drawings, which are not necessarily drawn to scale, and wherein:

FIG. 1 illustrates formation of open alpha chains derived from collagen monomers;

FIG. 2A illustrates the effect of the association of the alpha chains with dextran;

FIG. 2B illustrates the behavior of the alpha chains without association of the dextran;

FIG. 3 illustrates the effect of other hydrogel matrix additives;

FIG. 4A illustrates a polyglycan immobilized to a surface of a medical device;

FIG. 4B illustrates a polyglycan immobilized to a surface of a medical device and a polypeptide associated with the polyglycan to form a hydrogel;

FIG. 5 illustrates graphically the effect of a hydrogel matrix in promoting cell aggregation;

FIG. 6 illustrates graphically the effect of a hydrogel matrix through induction of transforming growth factor beta 3;

FIG. 7 illustrates a polyglycan immobilized to a surface of a medical device through a terminal group and a polypeptide associated with the polyglycan to form a hydrogel;

FIG. 8 illustrates one method of forming an immobilized bioactive hydrogel matrix of the present invention; and FIG. 9 illustrates a covalently cross-linked hydrogel matrix.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The formulation of a thermoreversible hydrogel matrix providing a cell culture medium and composition for preserving cell viability is taught by U.S. Pat. No. 6,231,881, herein incorporated by reference in its entirety. Additionally, a hydrogel matrix useful in promoting vascularization is provided in U.S. Pat. No. 6,261,587, herein incorporated by reference in its entirety. The thermoreversible hydrogel matrix taught by these references is a gel at storage temperatures and molten at physiologic temperatures, and comprises a combination of a collagen-derived component, such as gelatin, a long chain polyglycan, such as dextran, and effective amounts of other components, such as polar amino acids. The thermoreversible hydrogel matrix taught by these references is discussed below in connection with FIGS. 1-3.

Collagen is a major protein component of the extracellular matrix of animals. Collagen is assembled into a complex fibrillar organization. The fibrils are assembled into bundles that form the fibers. The fibrils are made of five microfibrils placed in a staggered arrangement. Each microfibril is a collection of collagen rods. Each collagen rod is a right-handed triple-helix, each strand being itself a left-handed helix. Collagen fibrils are strengthened by covalent intra- and intermolecular cross-links which make the tissues of mature animals insoluble in cold water. When suitable treatments are used, collagen rods are extracted and solubilized where they keep their conformation as triple-helices. This is denatured collagen and differs from the native form of collagen, but has not undergone sufficient thermal or chemical treatment to break the intramolecular stabilizing covalent bonds found in collagen. When collagen solutions are extensively heated, or when the native collagen containing tissues are subjected to chemical and thermal treatments, the hydrogen and covalent bonds that stabilize the collagen helices are broken, and the molecules adopt a disordered conformation. By breaking these hydrogen bonds, the polar amine and carboxylic acid groups are now available for binding to polar groups from other sources or themselves. This material is gelatin and is water-soluble at 40-45° C.

As noted above, gelatin is a form of denatured collagen, and is obtained by the partial hydrolysis of collagen derived from the skin, white connective tissue, or bones of animals. Gelatin may be derived from an acid-treated precursor or an alkali-treated precursor. Gelatin derived from an acid-treated precursor is known as Type A, and gelatin derived from an alkali-treated precursor is known as Type B. The macromolecular structural changes associated with collagen degradation are basically the same for chemical and partial thermal hydrolysis. In the case of thermal and acid-catalyzed degradation, hydrolytic cleavage predominates within individual collagen chains. In alkaline hydrolysis, cleavage of inter- and intramolecular cross-links predominates.

FIG. 1 illustrates the hydrolytic cleavage of the tropocollagen 10, forming individual polar alpha chains of gelatin 15. Heating tropocollagen 10 disrupts the hydrogen bonds that tightly contain the triple stranded monomers in mature collagen.

FIGS. 2A-2B illustrate stabilization of the matrix monomeric scaffolding by the introduction of a long-chain polyglycan, such as dextran 20. As depicted in FIG. 2A, the dextran 20 serves to hold open the gelatin 15, that has been previously heated, by interfering with the natural predisposition of the gelatin 15 to fold upon itself and form hydrogen bonds between its polar groups. In the absence of dextran 20, as shown in FIG. 2B, when the gelatin 15 begins to cool, it will form hydrogen bonds between the amino and carboxylic acid groups within the linear portion of the monomer and fold upon itself, thus limiting available sites for cellular attachment.

The thermoreversible matrix contains a polyglycan, such as dextran, at a therapeutically effective concentration ranging from, for example, about 0.01 to about 10 mM, preferably about 0.01 to about 1 mM, most preferably about 0.01 to about 0.1 mM. In one embodiment, dextran is present at a concentration of about 0.09 mM.

The thermoreversible matrix also contains gelatin, at a therapeutically effective concentration ranging from, for example, about 0.01 to about 40 mM, preferably about 0.05 to about 30 mM, most preferably about 1 to 5 mM. Advantageously, the gelatin concentration is approximately 1.6 mM.

In order to increase cell binding, intact collagen may be added in small amounts to the thermoreversible matrix in order to provide additional structure for the cells contained in the matrix. The final concentration of intact collagen is from about 0 to about 5 mM, preferably about 0 to about 2 mM, most preferably about 0.05 to about 0.5 mM. In one embodiment, the concentration of intact collagen is about 0.11 mM.

The thermoreversible matrix may additionally contain an effective amount of polar amino acids, which are commonly defined to include tyrosine, cysteine, serine, threonine, asparagine, glutamine, asparatic acid, glutamic acid, arginine, lysine, and histidine. For application in the present invention, the amino acids are preferably selected from the group consisting of cysteine, arginine, lysine, histidine, glutamic acid, aspartic acid and mixtures thereof, or derivatives or analogues thereof. By amino acid is intended all naturally occurring alpha amino acids in both their D and L stereoisomeric forms, and their analogues and derivatives.

An analog is defined as a substitution of an atom or functional group in the amino acid with a different atom or functional group that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine. The total concentration of all polar amino acids is generally between about 3 to about 150 mM, preferably about 10 to about 65 mM, and more preferably about 15 to about 40 mM.

Advantageously, the added polar amino acids comprise L-cysteine, L-glutamic acid, L-lysine, and L-arginine. The final concentration of L-glutamic acid is generally about 2 to about 60 mM, preferably about 5 to about 40 mM, most preferably about 10 to about 20 mM. In one embodiment, the concentration of L-glutamic acid is about 15 mM. The final concentration of L-lysine is generally about 0.5 to about 30 mM, preferably about 1 to about 15 mM, most preferably about 1 to about 10 mM. In one embodiment, the concentration of L-lysine is about 5.0 mM. The final concentration of L-arginine is generally about 1 to about 40 mM, preferably about 1 to about 30 mM, most preferably about 5 to about 15 mM. In one embodiment, the final concentration of arginine is about 10 mM. The final concentration of L-cysteine, which provides disulfide linkages, is generally about 5 to about 500 µM, preferably about 10 to about 100 µM, most preferably about 15 to about 25 µM. In one embodiment, the final concentration of cysteine is about 20 µM.

The thermoreversible matrix is preferably based upon a physiologically compatible buffer, one embodiment being Medium 199, a common nutrient solution used for in vitro culture of various mammalian cell types (available commercially from Sigma Chemical Company, St. Louis, Mo.), which is further supplemented with additives and additional amounts of some medium components, such as supplemental amounts of polar amino acids as described above.

Advantageously, aminoguanidine may be added to this formulation; however, other L-arginine analogues may also be used in the present invention, such as N-monomethyl L-arginine, N-nitro-L-arginine, or D-arginine. The final concentration of aminoguanidine is generally about 5 to about 500 µM, preferably about 10 to about 100 µM, most preferably about 15 to about 25 µM. In one embodiment, the final concentration is about 20 µM.

Additionally, the matrix may include one or more divalent cation chelators, which increase the rigidity of the matrix by forming coordinated complexes with any divalent metal ions present. The formation of such complexes leads to the increased rigidity of the matrix by removing the inhibition of hydrogen bonding between —$NH_2$ and —COOH caused by the presence of the divalent metal ions. A preferred example of a divalent cation chelator that is useful in the present invention is ethylenediaminetetraacetic acid (EDTA) or a salt thereof. The concentration range for the divalent cation chelator, such as EDTA, is generally about 0.01 to about 10 mM, preferably 1 to about 8 mM, most preferably about 2 to about 6 mM. In a one embodiment, EDTA is present at a concentration of about 4 mM.

FIG. 3 illustrates the effect of polar amino acids and L-cysteine added to stabilize the units 25, formed by the gelatin 15 and dextran 20, by linking the exposed monomer polar sites to, for example, arginine's amine groups or glutamic acid's carboxylic acid groups. Furthermore, disulfide linkages can be formed between L-cysteine molecules (thereby forming cystine), which in turn form hydrogen bonds to the gelatin 15.

The mechanical and thermal characteristics of the thermoreversible hydrogel described above are to a large extent determined by the thermomechanical properties of one of its major components, gelatin. Gelatin-based matrices typically are molten at near physiologic temperatures and hence cannot be expected to have the requisite durability and mechanical properties when required for implantation as a medical device in certain applications. Therefore, it is imperative to stabilize these gels through a variety of intermolecular interactions including hydrogen bonding, electrostatic or polar amino acid mediated bonding, hydrophobic bonding and covalent bonding. Although not wishing to be bound by theory, it is believed that the types of bonding mechanisms described above in association with a polyglycan stabilize polypeptides such as gelatin. For example, as discussed in more detail below, the positively charged polar groups of the collagen-derived alpha chains are then able to associate with the negatively charged hydroxyl groups of the repeating glucose units found in, for example, dextran. The gelatin and dextran form a composite bioactive hydrogel containing macromolecular proteoglycan-type structures.

Unlike the prior art thermoreversible matrix discussed above, the present invention provides stabilized compositions comprising an immobilized bioactive matrix that can be used, for example, as a coating for implanted medical devices to modulate localized wound healing around an implanted medical device, or to produce a localized vasculogenic response and encourage tissue integration with the implanted device. The present invention is also directed to a method for manufacturing an immobilized bioactive coating or film of cell scaffolding material directly on a substrate surface, such as the surface of a medical device. The present invention provides a cell attachment scaffold that supports the initiation of a series of cell signaling pathways and modulates the localized wound healing and acute inflammatory cascade in response to the implanted foreign material. By "bioactive" is intended the ability to facilitate or discourage a cellular or tissue response of a host to implanted materials. Examples include, but are not limited to, induction of vasculogenesis, inhibition of the formation of a foreign body response, controlled tissue reorganization around an implanted material or medical device, promotion of cellular adhesion, or regeneration of specific anatomic features such as dermal pegs and rete ridges during dermal healing. The term "stabilized" or "stable" is intended to refer to compositions that are water-swellable, poorly soluble, solid or semi-solid materials at physiological temperature (i.e., about 37° C.) and in physiological fluids (e.g., aqueous body fluids having a physiological pH of about 7.4), which remain present in the host for sufficient time to achieve the intended response.

It is not believed that the immobilized or cross-linked bioactive matrix coating affects the intrinsic material or chemical properties of the underlying substrate (e.g., a medical device). Unlike prior art devices or hydrogels, the present invention is believed to modulate the acute response of a host animal to polymeric materials typically used for medical device manufacture, not by changing the material's properties, but rather by changing the localized tissue response to the implanted material.

The bioactive coatings of the invention can be applied to a surface of any substrate where such coatings would be useful. In particular, suitable substrates include medical devices. By medical device is intended to include any device, whether active or passive in nature, which may be inserted or implanted into a host organism, such as a mammal. The term "medical device" is further intended to encompass any natural or synthetic device or material, including nucleic acids, which is used therapeutically either in vivo, such as by implantation into a human or animal, or ex vivo to provide therapeutic benefit, whether intended to be a permanent implant or temporary implant. Such devices include but are not limited to catheters, artificial arteries, artificial organs, medical devices containing cells of either engineered tissues or isolated tissue fragments or cells derived from naturally occurring or genetically engineered sources, ligament replacements, bone replacements, glucose sensors, coronary pacemakers, lap-bands, monitors, artificial larynxes, prostheses (such as testicular, esophageal, tracheal, and fallopian tube), brain stimulators, bladder pacemakers, bladder stimulators, shunts, stents, tubes, defibrillators, cardioverters, heart valves, joint replacements, fixation devices, ocular implants, cochlear implants, breast implants, neurostimulators, bone growth stimulators, vascular grafts, muscle stimulators, left ventricular assist devices, pressure sensors, vagus nerve stimulators, drug delivery systems, sutures, staples, cell scaffolding materials, active or passive medical devices comprised of gels, pastes or solids and the like and ex vivo bioreactors for liver, kidney or other organ support devices. Ex vivo bioreactors are external to the patient's body and used temporarily to provide metabolic function pending organ transplantation or other therapeutic intervention. Any foreign object that is placed in the body, or in contact with body tissues or fluids whether for a temporary time period or permanently, may benefit from the present invention.

The medical device of the present invention may be rigid or flexible, solid, fibrillar, or woven and may be derived from naturally occurring materials or constructed from synthetic materials. Exemplary materials of construction include acrylates, polyglycolic-polylactic acid copolymers, polyhydroxybutyrates, polyesters (such as Dacron®), expanded polytetrafluoroethylene (ePTFE), bioactive glass, ceramics (such as hydroxyapatites), coralline materials, processed tissue (such as demineralized bone), polycarbonate, polyurethane/polycarbonate copolymers, metals (such as titanium), and mixtures, composites or subassemblies thereof. Bioactive glasses generally contain silicon dioxide ($SiO_2$) as a network former and are characterized by their ability to firmly attach to living tissue. Examples of bioactive glasses available commercially and their manufacturers include Bioglass® (American Biomaterials Corp., USA, 45% silica, 24% calcium oxide (CaO), 24.5% disodium oxide ($Na_2O$), and 6% pyrophosphate ($P_2O_5$)), Consil® (Xeipon Ltd., UK), NovaBone® (American Biomaterials Corp.), Biogran® (Orthovita, USA), PerioGlass® (Block Drug Co., USA), and Ceravital® (E. Pfeil & H. Bromer, Germany). Corglaes® (Giltech Ltd., Ayr, UK) represents another family of bioactive glasses containing pyrophosphate rather than silicon dioxide as a network former. These glasses contain 42-49 mole % of $P_2O_5$, the remainder as 10-40 mole % as CaO and $Na_2O$.

The term "subassemblies" is intended to encompass multiple piece construction of the device, wherein the individual pieces of the device are constructed of the same or different materials. The term "composite" is intended to encompass devices comprising different active or passive materials, present to meet specific design requirements for the intended medical device.

The present invention provides a stabilized bioactive matrix layer or coating that overlies an exposed surface of a medical device or other substrate and is immobilized thereon. As the present invention is useful as a coating for any portion of a medical device that may have contact with body tissues or fluids, either in vivo or ex vivo, both temporarily and permanently, the term "exposed surface" is intended to encompass any such surface of a medical device that is exposed to brief or prolonged contact with body tissues or fluids. The word "surface" as used throughout in reference to a medical device or other substrate is therefore intended to encompass, in particular, any surface of the medical device operatively positioned for exposure to body tissues or fluids.

The matrix layer is formed from at least two high molecular weight components. The high molecular weight components of the bioactive hydrogel matrix are selected from the group consisting of high molecular weight polyglycans, high molecular weight polypeptides, and combinations thereof. By high molecular weight polyglycan is intended any polysaccharide consisting of more than about 10 monosaccharide residues joined to each other by glycosidic linkages. The polyglycan may consist of the same monosaccharide residues, or various monosaccharide residues or derivatives of monosaccharide residues. Dextran, a preferred polysaccharide, typically comprises linear chains of $\alpha(1\rightarrow6)$-linked D-glucose residues, often with $\alpha(1\rightarrow2)$- or $\alpha(1\rightarrow3)$-branches. Native dextran, produced by a number of species of bacteria of the family Lactobacilliaceae, is a polydisperse mixture of components.

The polyglycan component preferably has a molecular weight range of about 2,000 to about 8,000,000 Da, more preferably about 20,000 to about 1,000,000 Da. Unless otherwise noted, molecular weight is expressed herein as number average molecular weight ($M_n$), which is defined as $$\frac{\sum NiMi}{\sum Ni},$$

wherein Ni is the number of polymer molecules (or the number of moles of those molecules) having molecular weight Mi.

Any polysaccharide, including glycosaminoglycans (GAGs) or glucosaminoglycans, with suitable viscosity, molecular mass and other desirable properties may be utilized in the present invention. By glycosaminoglycan is intended any glycan (i.e., polysaccharide) comprising an unbranched polysaccharide chain with a repeating disaccharide unit, one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. By glucosaminoglycan is intended any glycan (i.e. polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate.

By high molecular weight polypeptide is intended any tissue-derived or synthetically produced polypeptide, such as collagens or collagen-derived gelatins. Although collagen-derived gelatin is the preferred high molecular weight polypeptide component, other gelatin-like components characterized by a backbone comprised of sequences of amino acids having polar groups that are capable of interacting with other molecules can be used. For example, keratin, decorin, aggrecan, glycoproteins (including proteoglycans), and the like could be used to produce the polypeptide component. In one embodiment, the polypeptide component is porcine gelatin from partially hydrolyzed collagen derived from skin tissue. Polypeptides derived from other types of tissue could also be used. Examples include, but are not limited to, tissue extracts from arteries, vocal chords, pleura, trachea, bronchi, pulmonary alveolar septa, ligaments, auricular cartilage or abdominal fascia; the reticular network of the liver; the basement membrane of the kidney; or the neurilemma, arachnoid, dura mater or pia mater of the nervous system. Purified polypeptides including, but not limited to, laminin, nidogen, fibulin, and fibrillin or protein mixtures such as those described by U.S. Pat. No. 6,264,992 and U.S. Pat. No. 4,829,000, extracts from cell culture broth as described by U.S. Pat. No. 6,284,284, submucosal tissues such as those described in U.S. Pat. No. 6,264,992, or gene products such as described by U.S. Pat. No. 6,303,765 may also be used. Another example of a suitable high molecular weight polypeptide is a fusion protein formed by genetically engineering a known reactive species onto a protein. The polypeptide component preferably has a molecular weight range of about 3,000 to about 3,000,000 Da, more preferably about 30,000 to about 300,000 Da.

In a preferred embodiment, gelatin and dextran are components of the bioactive matrix of the present invention. For ease of describing the invention, the terms "gelatin" and "dextran" are used throughout with the understanding that various alternatives as described above, such as other polyglycan and polypeptide components readily envisioned by those skilled in the art, are contemplated by the present invention.

FIG. 4A illustrates one embodiment of the present invention wherein a high molecular weight component of the matrix 20, such as a polysaccharide (e.g., dextran), is immobilized to an exposed surface 30 of a medical device 60. In this embodiment, the high molecular weight component 20 is attached to the exposed surface 30 via a plurality of covalent linkages 40, such as peptide linkages, between the exposed surface 30 of the medical device 60 and pendant reactive groups along the high molecular weight component chain 20. In this manner, a high molecular weight component of the matrix, such as either dextran or gelatin, can be covalently attached to an exposed surface 30 of a medical device 60 to form an immobilized coating.

In this particular embodiment, the surface of the medical device must first be activated. Surface activation of synthetic materials is well known to those skilled in the art of surface modification. For example, surface activation methods are commonly used for the immobilization of biomacromolecules during the preparation of affinity chromatography media. Common surface modification techniques are outlined in *Affinity Chromatography: A Practical Approach*, Dean et al., IRL Press, 1985 ISBN 0-904147-71-1, which is incorporated by reference in its entirety. Other methods of preparing synthetic or naturally derived surfaces for subsequent reaction with macromolecular species in solution are well-known to those skilled in the art.

In one embodiment, reactive amine groups are formed on the surface. For example, perfluorinated poly(ethylene-co-propylene) tape (Teflon®) and poly(ethylene terephthalate)

(PET) sheets can be coated with thin amine polymer layers deposited from a "monomer" vapor of volatile amines using a radio-frequency glow discharge. The density of the formed amine layer can be varied by selecting appropriate volatile amines. In one particular study, low amine density films were prepared using n-heptylamine, while high amine density films were prepared using allylamine (See, Kingshott et al., "Effects of cloud-point grafting, chain length, and density of PEG layers on competitive adsorption of ocular proteins" Biomaterials 23:2043-2056 (2002)). The carboxyl groups of activated dextran or gelatin react with the available amine groups of the surface, to form a Schiff base which can then be further reduced using either sodium borohydride or sodium cyanoborohydride to form peptide links. The high molecular weight component is thus immobilized on the surface of the medical device by covalent linkages therebetween.

The extent and uniformity of surface coverage by the immobilized high molecular weight components can be varied using reaction parameters well known to those skilled in the art. Similarly, by varying the concentration of reactive species in solution above an activated surface, the thickness of the immobilized bioactive hydro gel may be controlled. For example, a thin uniform bioactive hydrogel coating may be desirable for the improved long-term function of an implanted glucose biosensor, where the intended device function requires rapid equilibration between the local tissue environment and the sensor interface for optimal performance. Such methods are well known to those skilled in the art. In another example, relatively thick bioactive hydrogel coatings may be desirable for medical devices requiring extensive tissue integration for optimal performance. Cell scaffolds or tissue bulking devices for sphincter repair and regeneration are examples of such medical devices which may benefit from a design composed of an underlying substrate coated with a bioactive hydrogel coating to provide both structural and mechanical tissue support while encouraging tissue integration and localized tissue regeneration. Using methods outlined above, one can construct bioactive hydrogel coatings ranging in thickness from about $10^{-4}$ to about 10 cm.

The immobilized dextran or gelatin component may be used as a template upon which a cell scaffolding material similar to the thermoreversible hydrogel matrix described above may be constructed. For example, at least one additional high molecular weight component (e.g., gelatin), and at least one enhancing agent may be added to the immobilized high molecular weight component (e.g., dextran) to form an immobilized bioactive hydrogel matrix on the surface of the medical device. The relative amounts of the various hydrogel ingredients may be varied to obtain a wide range of desirable therapeutic and biomechanical properties. In one embodiment, the same concentrations as used in the thermoreversible matrix formulation discussed above are used.

By "enhancing agent" or "stabilizing agent" is intended any compound added to the hydrogel matrix, in addition to the two high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent can include any compound, especially polar compounds, that, when incorporated into the cross-linked hydrogel matrix, enhances the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as EDTA or salts thereof. Polar amino acids is intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular enhancing agent are the same as noted above in connection with the thermoreversible hydrogel matrix. Polar amino acids, EDTA, and mixtures thereof, are preferred enhancing agents. The enhancing agents can be added to the matrix composition before, during, or after immobilization of a high molecular weight component to the surface of the medical device.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

For example, aggregation of human fibroblasts exposed to bioactive hydrogels has been observed, while aggregation is not observed when fibroblasts are exposed to the individual components of the bioactive hydrogel. Results from numerous (over fifty) controlled experiments have shown that normal neonatal human skin fibroblasts form multi-cell aggregates when exposed to the complete thermoreversible hydrogel formulation at 37° C., while no such cell aggregating activity is demonstrated using formulations in which the bioactive copolymer is not formed. The aggregated cells form tightly apposed cell clusters with interdigitating cytoplasmic processes, while cells treated with formulations lacking the copolymer remain round and without surface projections. As shown in FIG. 5, in a sample of human fibroblasts exposed to a bioactive hydrogel comprising dextran and gelatin, at least 80% of the cells present were in an aggregated state while less than 20% of the cells present remained as single cells. The opposite effect was observed in samples where the human fibroblasts were exposed to collagen monomer alone, carbohydrate alone, or were left untreated. In samples exposed to collagen monomer alone, approximately 75% of the cells remained in a single cell configuration while only about 25% of the cells were in an aggregated state. Nearly the same effect was observed in samples exposed to carbohydrate alone. In samples that were left untreated, approximately 60% of the cells remained in a single cell state while only about 40% of the cells were in an aggregated state.

In a preferred embodiment, dextran is immobilized on an exposed surface of the device and gelatin is added, thereby forming a copolymer with the dextran through hydrogen bonding and polar interactions. This embodiment is shown in FIG. 4B where dextran 20, having gelatin 15 associated therewith, is immobilized on an exposed surface 30 of a medical device 60. These interactions may then be further stabilized through subsequent covalent bonding mediated by added reactive species (i.e., enhancing agents). The finished product is a stabilized, bioactive hydrogel which functions as a cell attachment scaffold having a localized effect on cellular responses, thereby improving the long-term performance of the medical device.

One such effect on cellular response is illustrated in FIG. 6, which provides a graphical representation of the results of one study of gene expression in normal human neonatal skin fibroblasts. That study demonstrated a marked induction of transforming growth factor beta 3 (TGF-β3) following hydrogel exposure. Expression of this gene is associated with scarless wound healing as seen during fetal development. Conversely, in the same cells, transforming growth factor beta 1 (TGF-β1), which is instrumental in scar formation during adult wound healing, was not induced by hydrogel exposure reflecting the ability of the hydrogel to facilitate a specific character of response in a population of tissue cells.

In this embodiment, where dextran is immobilized on the surface and gelatin is added, the dextran, containing predominantly relatively unreactive hydroxyl groups, requires activation to convert the hydroxyl groups to the more reactive aldehyde groups suitable for cross-linking to the surface. This must be done prior to contacting the surface of the medical device, which has previously undergone surface modification, such as by the method described above for forming reactive amine groups. For instance, the dextran, or other polyglycan component, can be modified, such as by oxidation, in order to cross-link with the modified surface of the medical device. One known reaction for oxidizing polysaccharides is periodate oxidation. The basic reaction process utilizing periodate chemistry is well known and appreciated by those skilled in the art. Periodate oxidation is described generally in *Affinity Chromatography: A Practical Approach*, Dean, et al., IRL Press, 1985 ISBN0-904147-71-1. The oxidation of dextran by the use of periodate-based chemistry is described in U.S. Pat. Nos. 3,947,352 and 6,011,008, which are herein incorporated by reference in their entirety.

In periodate oxidation, hydrophilic matrices may be activated by the oxidation of the vicinal diol groups. With a cellulosic surface, or other polysaccharide surface, this is generally accomplished through treatment with an aqueous solution of a salt of periodic acid, such as sodium periodate ($NaIO_4$), which oxidizes the sugar diols to generate reactive aldehyde groups (e.g. dialdehyde residues). This method is a rapid, convenient alternative to other known oxidation methods, such as those using cyanogen bromide. Materials activated by periodate oxidation may be stored at 4° C. for several days without appreciable loss of activity. This method can be used to prepare activated biomaterial surfaces appropriate for polypeptide binding or to prepare soluble activated polysaccharides to be bound to surfaces containing primary amine groups.

Periodate oxidized materials, such as dextran, readily react with materials containing amino groups, such as an activated surface of a medical device or a polypeptide, producing a cross-linked material through the formation of Schiff's base links. A Schiff base is a name commonly used to refer to the imine formed by the reaction of a primary amine with an aldehyde or ketone. The aldehyde groups formed on the cellulosic surface react with most primary amines between pH values from about 4 to about 6. The Schiff's base links form between the dialdehyde residues on the cellulosic surface and the free amino groups on the polypeptide or activated surface of the medical device. The cross-linked product may subsequently be stabilized (i.e. formation of stable amine linkages) by reduction with a borohydride, such as sodium borohydride ($NaBH_4$) or cyanoborohydride ($NaBH_3CN$). The residual aldehyde groups may be consumed with ethanolamine. Other methods known to those skilled in the art may be utilized to provide reactive groups on one of the high molecular weight components of the matrix.

The immobilized hydrogel matrix coatings of the present invention are biomimetic, meaning the coating layer imitates or stimulates a biological process or product. Some biomimetic processes have been in use for several years, such as the artificial synthesis of vitamins and antibiotics. More recently, additional biomimetic applications have been proposed, including nanorobot antibodies that seek and destroy disease-causing bacteria, artificial organs, artificial arms, legs, hands, and feet, and various electronic devices. The biomimetic scaffolding materials of the present invention may yield therapeutically useful surface coatings that are stable at about 37° C., or body temperature.

Once a high molecular weight component, such as dextran or gelatin, has been covalently cross-linked to the surface of the medical device, the second high molecular weight component can be added. The two high molecular weight components, one being covalently cross-linked to the surface of the medical device, interact through hydrogen bonding and polar attractions, thereby forming a stabilized copolymer. Additionally, at least one enhancing agent, as described above, can be added to further stabilize the hydrogel matrix.

Dextran or gelatin may be immobilized in a pendant, or chain-like, fashion to the surface of the medical device as shown in FIGS. 4A and 4B. This approach may be useful for the development of glucose sensors or other in-dwelling devices requiring improved soft tissue integration for long-term function and biocompatibility. This configuration may also be useful for guided tissue growth or as a means of modulating cell growth and structure within a three-dimensional tissue engineered construct such as a device intended to function as an artificial liver or kidney. The use of a bio-erodible bulk material allows one to fabricate engineered constructs either for controlled drug delivery with long-term release of a pharmaceutical agent to an induced vascular bed, or the development of guided tissue growth for bulking applications.

In another embodiment, the dextran 20 (or gelatin component) may be attached to the surface via a peptide link at one terminus of the dextran chain, as shown in FIG. 7. As with the embodiment shown in FIG. 4, the surface 30 of the device 60 must be activated using common surface modification methods as outlined above. One skilled in the art would readily understand the parameters necessary for immobilizing dextran at one terminus. (See for example, Larm, a et al., "A New Non-Thrombogenic Surface Prepared By Selective Covalent Binding Of Heparin Via A Modified Reducing Terminal Residue" *Biomat Med Dev Artif Organs* 11:161-73 (1983)). One skilled in the art would also readily understand the methods for immobilizing other macromolecules such as polypeptides via one terminus. (See for example, Gregorius, K. et al., "In Situ Deprotection: A Method For Covalent Immobilization Of Peptides With Well-Defined Orientation For Use In Solid Phase Immunoassays Such As Enzyme-Linked Immunosorbent Assay" *Anal Biochem* 29994-91(2001), and Olbrich K. C. et al., "Surfaces Modified With Covalently-Immobilized Adhesive Peptides Affect Fibroblast Population Motility" *Biomaterials* 17:144-153 (1996)). Those skilled in the art will further recognize that surface activation of substrates can achieve the same end of immobilizing one of the two high molecular weight components upon a surface without requiring modification of the native macromolecule. For example, surface immobilization of proteins to insoluble PVA substrates has been described previously (See, Manecke G. and Vogt, H. G., *J Solid Phase Biochem* 4(233) (1979)).

Dextran immobilization occurring through activated terminal groups forms "end-on" immobilized dextran, or "brush-like surfaces" as shown in FIG. 7. Here, the gelatin monomer 15 may then be formed around the immobilized dextran 20 to produce a biomimetic structure 80 designed to facilitate the activation of cell signaling pathways similar to those found during embryonic development. This configuration may lead to a more hydrogel-like surface and may provide a "softer" surface for guided cell growth. As with the pendant configuration, both permanent and bio-erodible surfaces may be modified in this manner. The extent of surface coverage by dextran is dependent on the molecular weight of the dextran and the extent of dextran branching.

FIG. 8 illustrates yet another embodiment, whereby gelatin is immobilized to the surface of a medical device. Gelatin with its native reactive primary amines distributed along the polypeptide backbone can be immobilized to surfaces containing aldehyde groups. Activated surfaces may be formed using radio frequency glow discharge treatment of polymeric surfaces in the presence of oxygen or other reactive oxidative species. This surface treatment forms aldehydes and other reactive species on the surface of the treated material, which can subsequently react with and immobilize gelatin directly. Gelatin may also form linkages, such as peptide linkages, with the surface of the device in a pendant fashion or only at a terminus of the gelatin chain. Gelatin is immobilized or tethered to a surface of a medical device at room temperature as shown in Step 1 of FIG. 8. Next, dextran is added and the temperature elevated to alter the gelatin quaternary structure to disrupt thermally stabilized intramolecular mediated hydrogen bonding producing a more open polypeptide conformation as shown in Step 2. For Step 2, the surface temperature should be elevated to at least about 30 to about 90° C., preferably about 40 to about 60° C. Various reactive species including, but not limited to, polar amino acids and amino acid derivatives as described earlier are also added and allowed to react at this step. Decreasing the temperature may further assist intermolecular interactions so that the dextran begins interacting with the gelatin as shown in Step 3. During Step 3, additional components, such as polar amino acids, can also be added to the matrix. Finally, in Step 4, the surface is once again at room temperature and a stabilized bioactive matrix coating is formed on the surface. The resulting matrix is a tightly bonded gelatin/dextran bioactive hydrogel matrix. Subsequent post-processing steps may include washing to remove excessive reactive species from the stabilized hydrogel. Typically, the temperature of the surface of the medical device varies from about 20 to about 60° C. during the above-described steps. The pH range for the copolymer formation, as described above, is within the physiologic range, preferably between about 6 and about 8, most preferably between about 7 and about 7.6.

Another method useful for immobilizing macromolecules, such as gelatin or dextran, to a surface is by way of a mechanical process. For example, a synthetic thermoplastic polymer may be partially swollen in the presence of a fluid containing a polymer solvent dispersed in water. The addition of macromolecules to this fluid allows the added solutes to become entrapped within the open, swollen surface of the polymer. By rapidly exchanging the fluid phase surrounding the swollen polymer, the polymer de-swells, entrapping the added macromolecular solutes within the surface of the polymer.

In yet another embodiment, bioactive hydrogels may be formed directly using electrooxidation. In this method, a molten thermoreversible hydrogel is placed in an electrolytic cell containing two conductive electrodes. A potential difference is applied between the electrodes, and oxidizable species in solution (i.e. functional groups such as hydroxyls, and amines) are directly oxidized at the anode. The resulting reactive oxidized compounds condense at the anodic surface to form a water-insoluble hydrogel coating. In this manner, for example, titanium mesh commonly used for craniofacial reconstructive surgery can be coated with an immobilized bioactive hydrogel to direct tissue organization and vascularization at the site of the implant.

Additional methods for immobilizing macromolecules are known in the art and include the methods described in the following references, each of which is incorporated by reference in its entirety: (i) Puleo D. A. et al., "A technique to immobilize bioactive proteins, including bone morphogenetic protein-4 (BMP-4), on titanium alloy" *Biomaterials*, 23:2079-2087 (2002); (ii) Kong, U. et al., "Durable Surface Modification of Poly(tetrafluoroethylene) by Low Pressure $H_2O$ Plasma Treatment Followed by Acrylic Acid Graft Polymerization" *Coll Surf B: Biointerface* 24:63-71 (2002); (iii) Chandy, T. et al., "Use of Plasma Glow for Surface Engineering Biomolecules to Enhance Blood Compatibility of Dacron and PTFE Vascular Prostheses" *Biomaterials* 21:699-712 (2000); (iv) Bos, G. W. et al., "Proliferation of Endothelial Cells on Surface-Immobilized Albumin-Heparin Conjugate Loaded with Basic Fibroblast Growth Factor" *J Biomed Mater Res* 44:330-340 (1999); (v) Ayhan F. et al., "Optimization of Urerase[sic] Immobilization onto Non-Porous HEMA Incorporated Poly(EGDMA) Microbeads and estimation of kinetic parameters" *Biores Technol* 81:131-40 (2002); (vi) Massia S. P. et al., "Surface Immobilized Dextran Limits Cell Adhesion and Spreading" *Biomaterials* 21:2253-2261 (2000); (vii) Barie, N. et al., "Covalent Photo-Linker Mediated Immobilization Of An Intermediate Dextran Layer To Polymer-Coated Surfaces For Biosensing Applications" *Bios Bioelect* 13:855-860 (1998); (viii) Chevolot, Y., et al., "Immobilization On Polysytrene Of Diazirine Derivatives Of Mono- And Disaccharides: Biological Activities Of Modified Surfaces" *Bioorganic & Med Chem* 9:2943-53 (2001); (ix) Tsai, C. C. et al., "Effects Of Heparin Immobilization On The Surface Characteristics Of A Biological Tissue Fixed With A Naturally Occurring Crosslinking Agent (Genipin) An In Vitro Study" *Biomaterials* 22:523-33 (2001); (x) Ito, Y., "Micropattern Immobilization Of Polysaccharide" *J Bioinorg Chem* 79:88-81 (2000); (xi) Massia, S. P. et al., "Immobilized rgd Peptides On Surface-Grafted Dextran Promote Biospecific Cell Attachment" *J Biomed Mater Res* 56:390-399 (2001); and (xii) Dai L., et al., "Biomedical Coatings By Covalent Immobilization Of Polysaccharides Onto Gas-Plasma-Activated Polymer Surfaces" *Surf Interface Anal* 29:46-55 (2000).

In yet another embodiment of the present invention, the two high molecular weight components of the hydrogel matrix surface coating may be cross-linked. As when crosslinking the dextran, or another polyglycan, to the modified surface of the medical device, the dextran must also first be modified in order to cross-link with the gelatin component. For example, partial oxidation of dextran using sodium meta-periodate produces a polyaldehyde dextran that can be immobilized on amine derivatized surfaces. Dextran immobilization in the presence of sodium cyanoborohydride catalytically reduces the formed Schiff base to the more stable amide covalent bond. The immobilized dextran coated substrate can then be washed to remove the excess reagents, and treated with sodium meta-periodate to form additional aldehydes. This tethered polyaldehyde dextran can then cross-link with another high molecular weight component, such as gelatin.

The presence of cross-linking between the two high molecular weight components of the hydrogel coating is illustrated in FIG. 9. As shown, in addition to being covalently attached to the exposed surface of the medical device, the dextran 20 can be covalently crosslinked to gelatin 15 by linkages 70, thereby forming a crosslinked network 50. The linkages 70 either result from reaction of functional groups on the gelatin 15 with functional groups on the dextran 20, or result from reaction of a bifunctional crosslinker molecule with both the dextran 20 and gelatin 15. One method of crosslinking gelatin and dextran is to modify the dextran molecules 20, such as by oxidation, in order to form functional groups suitable for covalent attachment to the gelatin 15. Dextran is modified, such as by oxidation, and stabilized via covalent bonding to gelatin 15, thereby forming a cross-linked network 50.

As noted above, periodate oxidation is one example of a known reaction for oxidizing polysaccharides that can also be used in this embodiment of the present invention in addition to other embodiments described previously. The reaction scheme can be carried out as before, oxidizing the sugar diols of the polyglycan, thereby forming reactive aldehyde groups. In this embodiment, the Schiff's base links form between the reactive aldehyde groups and the free amino groups on the polypeptide component of the hydrogel matrix. The cross-linked product may then be stabilized (i.e. formation of stable amine linkages) by reduction with a borohydride, such as sodium borohydride ($NaBH_4$) or cyanoborohydride ($NaBH_3CN$), and the residual aldehyde groups may be consumed with ethanolamine.

As an alternate method for forming the cross-linked hydrogel coating, a multifunctional cross-linking agent may be utilized as a reactive moiety that covalently links the gelatin and dextran chains. Such bifunctional cross-linking agents may include glutaraldehyde, epoxides (e.g. bis-oxiranes), oxidized dextran, p-azidobenzoyl hydrazide, N-[α-maleimidoacetoxy]succinimide ester, p-azidophenyl glyoxal monohydrate, Bis-[β-(4-azidosalicylamido)ethyl]disulfide (BASED), bis[sulfosuccinimidyl]suberate, dithiobis[succinimidyl propionate, disuccinimidyl suberate, 1-ethyl-3-[3-dimethylaminopropyl]carbodiimide hydrochloride, ethoxylated (20) trimethylpropane triacrylate, and other bifunctional cross-linking reagents known to those skilled in the art.

In one embodiment, 1.5 mL of a 0.5 mg/mL solution of Bis-[β-(4-azidosalicylamido)ethyl]disulfide (BASED) in dimethyl sulfoxide (DMSO), is added to a foil-wrapped vessel containing 15 mL of liquid thermoreversible hydrogel as described above. Photoactivated non-specific cross-linking of the thermoreversible hydrogel occurs upon exposure of the reactive mixture to long-wavelength light, such as that provided by continuous exposure to a 550 watt bulb (flood light used in photography). Longer exposure times demonstrated better cross-linking.

In another embodiment utilizing a cross-linking agent, polyacrylated materials, such as ethoxylated (20) trimethylpropane triacrylate, may be used as a non-specific photoactivated cross-linking agent. Components of an exemplary reaction mixture would include thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Continuous exposure of this reactive mixture to long-wavelength light (>498 nm) would produce a cross-linked hydrogel network.

In a further embodiment of the present invention, both high molecular weight components are cross-linked to the surface of the medical device. In this embodiment, the surface of the medical device must be activated prior to contacting the high molecular weight components. For example, bis-oxiranes, such as 1,4-butanediol diglycidoxy ether react readily with hydroxy- or amino-containing biomaterials at alkaline pH to yield derivatives which possess a long-chain hydrophilic, reactive oxirane (epoxide), which, in turn, can be reacted with amines, hydroxyls and other nucleophiles. Oxirane-coupled ligands are widely used and extremely stable and the use of a long chain bis-oxirane reagent introduces a long hydrophilic spacer molecule between the immobilized hydrogel components and the biomaterial surface which may be desirable in certain applications.

In another embodiment, the high molecular weight components may be modified in order to form reactive groups capable of reacting with the reactive groups of the activated surface of the medical device prior to contacting the surface of the medical device. This embodiment is not restricted by the order in which the high molecular weight components are contacted with the surface of the medical device. In one preferred embodiment, the surface of the medical device is activated, such as by radio frequency glow discharge in the presence of amine containing vapors to form reactive amine groups thereon, and modified dextran, such as oxidized dextran, is added. The dextran is covalently cross-linked to the surface of the medical device and gelatin is added. The gelatin is then also covalently cross-linked to the surface of the medical device through the polyaledehyde groups of the tethered dextran.

In another embodiment of the present invention, the surface of the medical device and the two high molecular weight components are all cross-linked to each other, wherein the polyglycan is covalently cross-linked to the surface of the medical device, the polypeptide is covalently cross-linked to the surface of the medical device, and the polyglycan and the polypeptide are cross-linked to each other. Various methods for carrying out this embodiment for coating a medical device would be envisioned by one skilled in the art. One possible method would comprise coating a polymeric medical device through radiation or electron beam grafting (See, Muzykewicz K. J. et al., "Platelet adhesion and contact activation time tests on HEMA coated cellulose acetate membranes" *J Biomed Mater Res.* 9(5): 487-99 (1975) and Venkataraman S. et al., "The reactivity of alpha-chymotrypsin immobilized on radiation-grafted hydrogel surfaces" *J Biomed Mater Res.* 11(1):111-23 (1977)).

The stabilized cross-linked bioactive hydrogel can be used to encourage site-specific tissue regeneration, including vasculogenesis, in the area surrounding an implanted medical device with the stabilized cross-linked bioactive hydrogel immobilized thereon. It is known in the art to use intact collagen, gelatin, or dextran as a carrier to hold and deliver growth factors and the like in methods designed to promote tissue growth. (See, for example, Kawai, K. et al., "Accelerated tissue Regeneration Through Incorporation of Basic Fibroblast Growth Factor-Impregnated Gelatin Microspheres into Artificial Dermis" *Biomaterials* 21:489-499

(2000); and Wissink, M. J. B. et al., "Binding and Release of Basic Fibroblast Growth Factor from Heparinized Collagen Matrices" *Biomaterials* 22:2291-2299 (2001)). By contrast, the intrinsic activity of the stabilized cross-linked hydrogel of the present invention is sufficient to elicit a specific sequence of biological responses, such as promoting tissue regeneration and vasculogenesis, without the addition of exogenous drugs or growth factors. In fact, the bioactive hydrogel matrix of the present invention can be substantially free, even completely free, of exogenous drugs or growth factors when used for vascularization or tissue regeneration. This intrinsically bioactive hydrogel, as a result of its unique structure, provides a cell attachment scaffold that modulates subsequent cellular activity, such as tissue regeneration and vasculogenesis.

The stabilized cross-linked hydrogel behaves similarly when used in other aspects of tissue regeneration. The hydrogel provides a stabilized structural lattice that facilitates cell retention and multiplication in areas with tissue damage. This is due in part to the intrinsic bioactivity of the hydrogel, which furthers the regenerative process. This is especially useful in applications where the success or functioning of an implanted medical device is dependent upon its integration with the surrounding tissue. The intrinsic bioactivity of the cross-linked hydrogel immobilized to the surface of the medical device not only reduces incidence of rejection by the host resulting from inflammatory response, immune response, etc., but it also increases healing and tissue regeneration in the site surrounding the implanted device.

The immobilized bioactive hydrogel matrix surface coating utilized in each of the embodiments described herein may be comprised solely of the two high molecular weight components. Preferably, each of the embodiments described herein incorporates additional components such as the enhancing agents utilized in the preferred embodiments described above. Table 1 below lists preferred components present within the immobilized bioactive hydrogel matrix surface coatings of the present invention along with suitable concentrations as well as preferred concentrations for each component. Note that the concentrations listed in Table 1 for gelatin and dextran would also be suitable for alternative polyglycan and polypeptide components.

TABLE 1

| Component | Concentration Range | Preferred Concentration |
| --- | --- | --- |
| L-glutamic acid | 2 to 60 mM | 15 mM |
| L-lysine | 0.5 to 30 mM | 5 mM |
| Arginine | 1 to 40 mM | 10 mM |
| Gelatin | 0.01 to 40 mM | 2 mM |
| L-cysteine | 5 to 500 µM | 20 µM |
| EDTA | 0.01 to 10 mM | 4 mM |
| Dextran | 0.01 to 10 mM | 0.1 mM |

As noted above, the present invention provides numerous benefits including eliciting vascularization at a localized site, modulating localized wound healing response, and providing suitable means of developing a retrievable cell implantation device for cell-based therapeutics. Additional benefits may include the following: reduced scarring associated with degradation of bioerodible suture materials; improvement in the performance and long-term function of extravascular sensors such as glucose sensors routinely used for insulin delivery systems; improvement in the rate of healing, durability, and mechanical properties around structural implants such as artificial joints and tendons; reduced pain and associated complications arising from post surgical adhesions especially during abdominal or spinal injury; and improved integration between natural tissues and implanted structures (i.e. teeth, porous hydroxyapatite or ceramic materials for bone repair).

EXPERIMENTAL

The present invention is more fully illustrated by the following examples, which are set forth to illustrate the present invention and are not to be construed as limiting thereof.

Example 1

A beaker with an internal volume of 50 mL was equipped with two copper electrodes at a 2.5 cm separation. The beaker was filled with an aqueous solution of liquid thermoreversible hydrogel containing dextran and gelatin. A potential difference of 18 V was applied across the cell. A hydrogel complex consisting of the covalently cross-linked thermoreversible hydrogel formulation immediately formed on the surface of the anode, and the thickness of the film increased with increasing time. The sterile hydrogel was insoluble in water at 37° C., was adherent to the underlying substrate and conformed to the surface of the anodic metal.

One skilled in the art would readily recognize the utility of this method for producing adherent hydrogel coatings on metallic substrates such as titanium meshes used for reconstructive surgery. Such bioactive hydrogel coatings are expected to improve the vascularity and osteointegration of the implant.

Example 2

Activated biomaterial surfaces suitable for having the hydrogel matrix cross-linked thereto can be prepared by copolymerization of monomers containing bifunctional groups, one of which is protected. For example, the monomer glycidyl methacrylate can be copolymerized using free radical initiation with other acrylates to form hydrogels, and hydrogel films. Poly(2-hydroxyethyl methacrylate-co-glycidyl methacrylate)-poly(HEMA-GMA) hydrogel films can be prepared by UV-initiated photopolymerization with α,α'-azoisobutyronitrile (AIBN) as an initiator, preferably under an inert atmosphere at 25° C. The epoxide content of the hydrogel films can be varied by varying the relative ratio of HEMA to GMA. For example, films with a high density of epoxides can be prepared by mixing 0.2 mL of HEMA, 0.8 mL GMA, 1 mL isopropyl alcohol, 10 mg AIBN (as a polymerization initiator), and 3.0 mL of 0.1M phosphate buffer (pH=7.0). The resulting mixture is stirred and equilibrated at 25° C. for 15 min in a thermostated water bath. The mixture can be then poured into the mold and exposed to long-wave ultraviolet radiation for 20 min. After polymerization, poly(HEMA-GMA) films can be washed several times with distilled water and cut into circular pieces with a biopsy punch. The functional epoxy group carrying poly(HEMA-GMA) film disks (10 g wet weight, diameter=1.0 cm) formed as described above are equilibrated in phosphate buffer (50 mM, pH=8.0) for 2 hours, and transferred to a container holding the thermoreversible hydrogel held at 39° C. Immobilization of the thermoreversible hydrogel to the surface of the biomaterial film can be carried out at 39° C. with frequent agitation. The poly(HEMA-GMA) films coated with a thermoreversible hydrogel can be removed and washed to remove non-covalently attached hydrogel materials.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed herein and that modifications and other embodiments are intended to be included within the scope of the appended claims. Although specific terms are employed herein, they are used in a generic and descriptive sense only and not for purposes of limitation.

That which is claimed:

1. A coated tissue supporting mesh comprising:
   a mesh implant having a surface and being adapted for providing one or both of structural and mechanical support to contacted tissue; and
   a hydrogel matrix comprising a polyglycan, a polypeptide comprising gelatin, and at least one enhancing agent selected from the group consisting of polar amino acids, divalent cation chelators, and combinations thereof;
   wherein the polyglycan is dextran or oxidized dextran;
   wherein the hydrogel matrix is solid or semi-solid at physiological temperature and physiological pH; and
   wherein the hydrogel matrix is overlying the surface of the mesh implant and is immobilized thereon.

2. The coated tissue supporting mesh according to claim 1, wherein the mesh is formed of a thermoplastic polymer.

3. The coated tissue supporting mesh according to claim 1, wherein the mesh is formed of a metallic material.

4. The coated tissue supporting mesh according to claim 1, wherein the polyglycan and polypeptide are covalently cross-linked to each other.

5. The coated tissue supporting mesh according to claim 1, wherein at least one of the polyglycan and the polypeptide is covalently cross-linked to the surface of the mesh implant.

6. A coated implant comprising:
   a flexible implant comprising a thermoplastic polymer and having a surface; and
   a hydrogel matrix comprising a polyglycan, a polypeptide comprising gelatin, and at least one enhancing agent selected from the group consisting of polar amino acids, divalent cation chelators, and combinations thereof;
   wherein the polyglycan is dextran or oxidized dextran;
   wherein the hydrogel matrix is solid or semi-solid at physiological temperature and physiological pH; and
   wherein the hydrogel matrix is overlying the surface of the flexible implant and is immobilized thereon.

7. The coated implant according to claim 6, wherein the implant is a mesh.

8. The coated implant according to claim 6, wherein the polyglycan and polypeptide are covalently cross-linked to each other.

9. The coated implant according to claim 6, wherein at least one of the polyglycan and the polypeptide is covalently cross-linked to the surface of the flexible implant.

* * * * *